US005700658A

United States Patent [19]
Kilgannon et al.

[11] Patent Number: 5,700,658
[45] Date of Patent: Dec. 23, 1997

[54] ICAM-4 MATERIALS AND METHODS

[75] Inventors: Patrick D. Kilgannon, Bothell; W. Michael Gallatin, Seattle, both of Wash.

[73] Assignee: ICOS Corporation, Bothell, Wash.

[21] Appl. No.: 245,295

[22] Filed: May 18, 1994

Related U.S. Application Data

[63] Continuation-in-part of Ser. No. 102,852, Aug. 5, 1993, abandoned, which is a continuation-in-part of Ser. No. 9,266, Jan. 22, 1993, abandoned, which is a continuation-in-part of Ser. No. 894,061, Jun. 5, 1992, abandoned, which is a continuation-in-part of Ser. No. 889,724, May 26, 1992, abandoned, which is a continuation-in-part of Ser. No. 827,689, Jan. 27, 1992, abandoned.

[51] Int. Cl.$^6$ .................................................. C12N 15/12
[52] U.S. Cl. .................. 435/69.1; 536/23.5; 435/320.1; 435/252.3; 435/325
[58] Field of Search ................ 536/23.5; 435/320.1, 435/252.3, 69.1, 325

[56] References Cited

FOREIGN PATENT DOCUMENTS

| | | |
|---|---|---|
| 0289949 | 9/1988 | European Pat. Off. . |
| 468257 A | 1/1992 | European Pat. Off. . |
| WO 89/02922 | 4/1989 | WIPO . |
| WO 90/13300 | 11/1990 | WIPO . |
| WO 91/10683 | 7/1991 | WIPO . |
| WO 91/16928 | 11/1991 | WIPO . |
| WO 92/04034 | 3/1992 | WIPO . |
| WO 92/06199 | 4/1992 | WIPO . |
| WO 93/14776 | 8/1993 | WIPO . |

OTHER PUBLICATIONS

Locus: MMU06483, Definition: Mus Musculus BALB/c Telencephalin Precurcor mRNA, Genbank–EMBL Database, Submitted 10 Feb. 1994.
Locus: Rabtelceph, Definition: Rabbit Telencephalin mRNA, Genbank–EMBL Sequence Database, 1994.
Ashkenazi, et al., *Proc.Natl.Acad.Sci.(USA)* 88:10535–10539 (1991) "Protection against endotoxic shock by tumor necrosis factor receptor immunoadhesin".
Capecchi, *Science* 244:1288–1292 (1989) "Altering the genome by homologous recombination."
Capon, et al., *Nature* 337:525–531 (1989) "Designing CD4 immunoadhesins for AIDS therapy."
de Fourgerolles, et al., *J.Exp.Med.* 175:185–190 (1992) "Intercellular adhesion molecule 3, a third adhesion counter–receptor for lymphocyte function associated molecule 1 on resting lymphocytes."
Dustin, et al., *J.Immunol.* 137:245–254 (1986) "Induction by IL–1 and interferon–γ: tissue distribution, biochemistry, and function of a natural adherence molecular (ICAM–1)".

Edwards, *Curr.Opin.Ther.Pat.* 1:1627–1630 (1991) "Cell adhesion molecules as a target for therapy."
Frohman, *PCR Protocols*, Innis (ed), pp.28–38 (1990) "RACE: rapid amplication of cDNA ends."
Imamura, et al., *Neurosci.Letts.* 119:118–121 (1990) "Variations by layers and developmental changes in expression of telencephalin."
Kita, et al., *Biochem.Biophys.Acta* 1131:108–110 (1992) "Sequence and expression of rt ICAM–1".
Mori, et al., *Proc.Natl.Acad.Sci.(USA)* 84:3921–3925 (1987) "Telencephalon–specific antigen identified by monoclonal antibody".
Newman, et al., *Science* 247:1219–1222 (1990) "PECAM–1 (CD31) cloning and relation to adhesion molecules of the immunoglobulin gene superfamily."
Oka, et al., *Neuroscience* 35:93–103 (1990) "Mammalian telencephalic neurons express a segment–specific membrane glycoprotein, telencephalin."
Sonderegger et al., *J.Cell Biol.* 119:1387–1394 (1992) "Regulation of axonal growth in the vertebrate nervous system by interactions between glycoproteins belonging to two subgroups of the immunoglobulin superfamily."
Springer, *Nature* 346:425–434 (1990) "Adhesion receptors of the immune systems."
Staunton, et al., *Nature* 339:61–64 (1989) "Functional cloning of ICAM–2, a cell adhesion ligand for LFA–1 homologous to ICAM–1."
Vonderheide, et al., *J.Cell.Biol* 125:215–222 (1994) "Residues within a conserved amino acid motif of domains 1 and 4 of VCAM–1 are required for binding to VLA–4".
Xu, et al., *J.Immunol.* 149:2560–2565 (1992) "Isolation, characterization, and expression of mouse ICAM–2 complementary and genomic DNA".
Yoshihara, et al., *Neurosci.Res.* 10:83–105 (1991) "Immunoglobulin superfamily molecules in the nervous system."
Yoshihiro, et al., *Neuron* 12:543–553 (1994) "An ICAM–related neuronal glycoprotein, telencephalin, with brain segment–specific expression".
Yoshihiro, et al., *Neuroscience* Supp. 18, p.S83 (1994) "Primary structure of telencephalon–specific neuronal adhesion molecule telencephalin."
Yoshihiro, et al., *Soc.Neurosci.Abstr.* 19 (1–3) p.646 (1993) "Telencephalin, a immunoglobulin superfamily."

*Primary Examiner*—Stephen Walsh
*Assistant Examiner*—Karen E. Brown
*Attorney, Agent, or Firm*—Marshall, O'Toole, Gerstein, Murray & Borun

[57] ABSTRACT

DNA sequences encoding a novel intercellular adhesion molecule polypeptide (designated "ICAM-4") and variants thereof are disclosed along with methods and materials for production of the same by recombinant procedures.

9 Claims, No Drawings

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 2988 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 61..2814

( x i ) SEQUENCE DESCRIPTION: SEQ ID NO:1:

```
AATTCGATCA  CTCGCGCTCC  CCTCGCCTTC  TGCGCTCTCC  CCTCCCTGGC  AGCGGCGGCA                60

ATG CCG GGG CCT TCA CCA GGG CTG CGC CGA ACG CTC CTC GGC CTC TGG                      108
Met Pro Gly Pro Ser Pro Gly Leu Arg Arg Thr Leu Leu Gly Leu Trp
 1               5                  10                  15

GCT GCC CTG GGC CTG GGG ATC CTA GGC ATC TCA GCG GTC GCG CTA GAA                      156
Ala Ala Leu Gly Leu Gly Ile Leu Gly Ile Ser Ala Val Ala Leu Glu
            20                  25                  30

CCT TTC TGG GCG GAC CTT CAG CCC CGC GTG GCG CTC GTG GAG CGC GGG                      204
Pro Phe Trp Ala Asp Leu Gln Pro Arg Val Ala Leu Val Glu Arg Gly
        35                  40                  45

GGC TCG CTG TGG CTC AAC TGC AGC ACT AAC TGT CCG AGG CCG GAG CGC                      252
Gly Ser Leu Trp Leu Asn Cys Ser Thr Asn Cys Pro Arg Pro Glu Arg
    50                  55                  60

GGT GGC CTG GAG ACC TCG CTA CGC CGA AAC GGG ACC CAG AGG GGT CTG                      300
Gly Gly Leu Glu Thr Ser Leu Arg Arg Asn Gly Thr Gln Arg Gly Leu
65                  70                  75                  80

CGC TGG CTG GCT CGA CAG CTG GTG GAC ATC CGA GAG CCT GAA ACC CAG                      348
Arg Trp Leu Ala Arg Gln Leu Val Asp Ile Arg Glu Pro Glu Thr Gln
                85                  90                  95

CCG GTC TGC TTC TTC CGC TGC GCG CGC CGC ACA CTC CAA GCG CGT GGG                      396
Pro Val Cys Phe Phe Arg Cys Ala Arg Arg Thr Leu Gln Ala Arg Gly
            100                 105                 110

CTC ATC CGA ACT TTC CAG CGA CCG GAT CGG GTA GAG CTA GTG CCT CTG                      444
Leu Ile Arg Thr Phe Gln Arg Pro Asp Arg Val Glu Leu Val Pro Leu
        115                 120                 125

CCT CCT TGG CAG CCT GTA GGT GAG AAC TTC ACC TTG AGC TGC AGG GTC                      492
Pro Pro Trp Gln Pro Val Gly Glu Asn Phe Thr Leu Ser Cys Arg Val
    130                 135                 140

CCG GGG GCA GGA CCC CGA GCG AGC CTC ACA TTG ACC TTG CTG CGA GGC                      540
Pro Gly Ala Gly Pro Arg Ala Ser Leu Thr Leu Thr Leu Leu Arg Gly
145                 150                 155                 160

GGC CAG GAG CTG ATT CGC CGA AGT TTC GTA GGC GAG CCA CCC GA GCT                        588
```

-continued

| | | | | | | | | | | | | | | | |
|---|---|---|---|---|---|---|---|---|---|---|---|---|---|---|---|
| Gly | Gln | Glu | Leu | Ile | Arg | Arg | Ser | Phe | Val | Gly | Glu | Pro | Pro | Arg | Ala |
| | | | | 165 | | | | 170 | | | | | 175 | | |

| CGG | GGT | GCG | ATG | CTC | ACC | GCC | ACG | GTC | CTG | GCG | CGC | AGA | GAG | GAT | CAC | 636 |
|---|---|---|---|---|---|---|---|---|---|---|---|---|---|---|---|---|
| Arg | Gly | Ala | Met | Leu | Thr | Ala | Thr | Val | Leu | Ala | Arg | Arg | Glu | Asp | His | |
| | | | 180 | | | | 185 | | | | | 190 | | | | |

| AGG | GCC | AAT | TTC | TCA | TGC | CTC | GCG | GAG | CTT | GAC | CTG | CGG | CCA | CAC | GGC | 684 |
|---|---|---|---|---|---|---|---|---|---|---|---|---|---|---|---|---|
| Arg | Ala | Asn | Phe | Ser | Cys | Leu | Ala | Glu | Leu | Asp | Leu | Arg | Pro | His | Gly | |
| | | 195 | | | | 200 | | | | 205 | | | | | | |

| TTG | GGA | CTG | TTT | GCA | AAC | AGC | TCA | GCC | CCC | AGA | CAG | CTC | CGC | ACG | TTT | 732 |
|---|---|---|---|---|---|---|---|---|---|---|---|---|---|---|---|---|
| Leu | Gly | Leu | Phe | Ala | Asn | Ser | Ser | Ala | Pro | Arg | Gln | Leu | Arg | Thr | Phe | |
| 210 | | | | | 215 | | | | | 220 | | | | | | |

| GCC | ATG | CCT | CCA | CTT | TCC | CCG | AGC | CTT | ATT | GCC | CCA | CGA | TTC | TTA | GAA | 780 |
|---|---|---|---|---|---|---|---|---|---|---|---|---|---|---|---|---|
| Ala | Met | Pro | Pro | Leu | Ser | Pro | Ser | Leu | Ile | Ala | Pro | Arg | Phe | Leu | Glu | |
| 225 | | | | | 230 | | | | | 235 | | | | | 240 | |

| GTG | GGC | TCA | GAA | AGG | CCG | GTG | ACT | TGC | ACT | TTG | GAT | GGA | CTG | TTT | CCT | 828 |
|---|---|---|---|---|---|---|---|---|---|---|---|---|---|---|---|---|
| Val | Gly | Ser | Glu | Arg | Pro | Val | Thr | Cys | Thr | Leu | Asp | Gly | Leu | Phe | Pro | |
| | | | | 245 | | | | 250 | | | | | 255 | | | |

| GCC | CCA | GAA | GCC | GGG | GTT | TAC | CTC | TCT | CTG | GGA | GAT | CAG | AGG | CTT | CAT | 876 |
|---|---|---|---|---|---|---|---|---|---|---|---|---|---|---|---|---|
| Ala | Pro | Glu | Ala | Gly | Val | Tyr | Leu | Ser | Leu | Gly | Asp | Gln | Arg | Leu | His | |
| | | | 260 | | | | | 265 | | | | | 270 | | | |

| CCT | AAT | GTG | ACC | CTC | GAC | GGG | GAG | AGC | CTT | GTG | GCC | ACT | GCC | ACA | GCT | 924 |
|---|---|---|---|---|---|---|---|---|---|---|---|---|---|---|---|---|
| Pro | Asn | Val | Thr | Leu | Asp | Gly | Glu | Ser | Leu | Val | Ala | Thr | Ala | Thr | Ala | |
| | | 275 | | | | | 280 | | | | | 285 | | | | |

| ACA | GCA | AGT | GAA | GAA | CAG | GAA | GGC | ACC | AAA | CAG | CTG | ATG | TGC | ATC | GTG | 972 |
|---|---|---|---|---|---|---|---|---|---|---|---|---|---|---|---|---|
| Thr | Ala | Ser | Glu | Glu | Gln | Glu | Gly | Thr | Lys | Gln | Leu | Met | Cys | Ile | Val | |
| 290 | | | | | 295 | | | | | 300 | | | | | | |

| ACC | CTC | GGG | GGC | GAA | AGC | AGG | GAG | ACC | CAG | GAA | AAC | CTG | ACT | GTC | TAC | 1020 |
|---|---|---|---|---|---|---|---|---|---|---|---|---|---|---|---|---|
| Thr | Leu | Gly | Gly | Glu | Ser | Arg | Glu | Thr | Gln | Glu | Asn | Leu | Thr | Val | Tyr | |
| 305 | | | | | 310 | | | | | 315 | | | | | 320 | |

| AGC | TTC | CCG | GCT | CCT | CTT | CTG | ACT | TTA | AGT | GAG | CCA | GAA | GCC | CCC | GAG | 1068 |
|---|---|---|---|---|---|---|---|---|---|---|---|---|---|---|---|---|
| Ser | Phe | Pro | Ala | Pro | Leu | Leu | Thr | Leu | Ser | Glu | Pro | Glu | Ala | Pro | Glu | |
| | | | | 325 | | | | | 330 | | | | | 335 | | |

| GGA | AAG | ATG | GTG | ACC | GTA | AGC | TGC | TGG | GCA | GGG | GCC | CGA | GCC | CTT | GTC | 1116 |
|---|---|---|---|---|---|---|---|---|---|---|---|---|---|---|---|---|
| Gly | Lys | Met | Val | Thr | Val | Ser | Cys | Trp | Ala | Gly | Ala | Arg | Ala | Leu | Val | |
| | | | 340 | | | | | 345 | | | | | 350 | | | |

| ACC | TTG | GAG | GGA | ATT | CCA | GCT | GCG | GTC | CCT | GGG | CAG | CCC | GCT | GAG | CTC | 1164 |
|---|---|---|---|---|---|---|---|---|---|---|---|---|---|---|---|---|
| Thr | Leu | Glu | Gly | Ile | Pro | Ala | Ala | Val | Pro | Gly | Gln | Pro | Ala | Glu | Leu | |
| | | 355 | | | | | 360 | | | | | 365 | | | | |

| CAG | TTA | AAT | GTC | ACA | AAG | AAT | GAC | GAC | AAG | CGG | GGC | TTC | TTC | TGC | GAC | 1212 |
|---|---|---|---|---|---|---|---|---|---|---|---|---|---|---|---|---|
| Gln | Leu | Asn | Val | Thr | Lys | Asn | Asp | Asp | Lys | Arg | Gly | Phe | Phe | Cys | Asp | |
| 370 | | | | | 375 | | | | | 380 | | | | | | |

| GCT | GCC | CTC | GAT | GTG | GAC | GGG | GAA | ACT | CTG | AGA | AAG | AAC | CAG | AGC | TCT | 1260 |
|---|---|---|---|---|---|---|---|---|---|---|---|---|---|---|---|---|
| Ala | Ala | Leu | Asp | Val | Asp | Gly | Glu | Thr | Leu | Arg | Lys | Asn | Gln | Ser | Ser | |
| 385 | | | | | 390 | | | | | 395 | | | | | 400 | |

| GAG | CTT | CGT | GTT | CTG | TAC | GCA | CCT | CGG | CTG | GAT | GAC | TTG | GAC | TGT | CCC | 1308 |
|---|---|---|---|---|---|---|---|---|---|---|---|---|---|---|---|---|
| Glu | Leu | Arg | Val | Leu | Tyr | Ala | Pro | Arg | Leu | Asp | Asp | Leu | Asp | Cys | Pro | |
| | | | | 405 | | | | | 410 | | | | | 415 | | |

| AGG | AGC | TGG | ACG | TGG | CCA | GAG | GGT | CCA | GAG | CAG | ACC | CTC | CAC | TGC | GAG | 1356 |
|---|---|---|---|---|---|---|---|---|---|---|---|---|---|---|---|---|
| Arg | Ser | Trp | Thr | Trp | Pro | Glu | Gly | Pro | Glu | Gln | Thr | Leu | His | Cys | Glu | |
| | | | 420 | | | | | 425 | | | | | 430 | | | |

| GCC | CGT | GGA | AAC | CCT | GAG | CCC | TCC | GTG | CAC | TGT | GCA | AGG | CCT | GAC | GGT | 1404 |
|---|---|---|---|---|---|---|---|---|---|---|---|---|---|---|---|---|
| Ala | Arg | Gly | Asn | Pro | Glu | Pro | Ser | Val | His | Cys | Ala | Arg | Pro | Asp | Gly | |
| | | 435 | | | | | 440 | | | | | 445 | | | | |

| GGG | GCG | GTG | CTA | GCG | CTG | GGC | CTG | TTG | GGT | CCA | GTG | ACC | CGT | GCC | CTC | 1452 |
|---|---|---|---|---|---|---|---|---|---|---|---|---|---|---|---|---|
| Gly | Ala | Val | Leu | Ala | Leu | Gly | Leu | Leu | Gly | Pro | Val | Thr | Arg | Ala | Leu | |
| | 450 | | | | | 455 | | | | | 460 | | | | | |

| GCG | GGC | ACT | TAC | CGA | TGT | ACA | GCA | ATC | AAT | GGG | CAA | GGC | CAG | GCG | GTC | 1500 |
|---|---|---|---|---|---|---|---|---|---|---|---|---|---|---|---|---|
| Ala | Gly | Thr | Tyr | Arg | Cys | Thr | Ala | Ile | Asn | Gly | Gln | Gly | Gln | Ala | Val | |
| 465 | | | | | 470 | | | | | 475 | | | | | 480 | |

| AAG | GAT | GTG | ACC | CTG | ACT | GTG | GAA | TAT | GCC | CCA | GCG | CTG | GAC | AGT | GTA | 1548 |

|  |  |
|---|---|
| Lys Asp Val Thr Leu Thr Val Glu Tyr Ala Pro Ala Leu Asp Ser Val<br>485              490              495 | |
| GGC TGC CCA GAA CGT ATT ACT TGG CTG GAG GGG ACA GAG GCA TCG CTT<br>Gly Cys Pro Glu Arg Ile Thr Trp Leu Glu Gly Thr Glu Ala Ser Leu<br>        500              505              510 | 1596 |
| AGC TGT GTG GCA CAC GGG GTC CCA CCA CCT AGC GTG AGC TGT GTG CGC<br>Ser Cys Val Ala His Gly Val Pro Pro Pro Ser Val Ser Cys Val Arg<br>            515              520              525 | 1644 |
| TCT GGA AAG GAG GAA GTC ATG GAA GGG CCC CTG CGT GTG GCC CGG GAG<br>Ser Gly Lys Glu Glu Val Met Glu Gly Pro Leu Arg Val Ala Arg Glu<br>        530              535              540 | 1692 |
| CAC GCT GGC ACT TAC CGA TGC GAA GCC ATC AAC GCC AGG GGA TCA GCG<br>His Ala Gly Thr Tyr Arg Cys Glu Ala Ile Asn Ala Arg Gly Ser Ala<br>545              550              555              560 | 1740 |
| GCC AAA AAT GTG GCT GTC ACG GTG GAA TAT GGT CCC AGT TTT GAG GAG<br>Ala Lys Asn Val Ala Val Thr Val Glu Tyr Gly Pro Ser Phe Glu Glu<br>            565              570              575 | 1788 |
| TTG GGC TGC CCC AGC AAC TGG ACT TGG GTA GAA GGA TCT GGA AAA CTG<br>Leu Gly Cys Pro Ser Asn Trp Thr Trp Val Glu Gly Ser Gly Lys Leu<br>        580              585              590 | 1836 |
| TTT TCC TGT GAA GTT GAT GGG AAG CCG GAA CCA CGC GTG GAG TGC GTG<br>Phe Ser Cys Glu Val Asp Gly Lys Pro Glu Pro Arg Val Glu Cys Val<br>        595              600              605 | 1884 |
| GGC TCG GAG GGT GCA AGC GAA GGG GTA GTG TTG CCC CTG GTG TCC TCG<br>Gly Ser Glu Gly Ala Ser Glu Gly Val Val Leu Pro Leu Val Ser Ser<br>    610              615              620 | 1932 |
| AAC TCT GGT TCC AGA AAC TCT ATG ACT CCT GGT AAC CTG TCA CCG GGT<br>Asn Ser Gly Ser Arg Asn Ser Met Thr Pro Gly Asn Leu Ser Pro Gly<br>625              630              635              640 | 1980 |
| ATT TAC CTC TGC AAC GCC ACC AAC CGG CAT GGC TCC ACA GTC AAA ACA<br>Ile Tyr Leu Cys Asn Ala Thr Asn Arg His Gly Ser Thr Val Lys Thr<br>            645              650              655 | 2028 |
| GTC GTC GTG AGC GCG GAA TCA CCG CCA CAG ATG GAT GAA TCC AGT TGC<br>Val Val Val Ser Ala Glu Ser Pro Pro Gln Met Asp Glu Ser Ser Cys<br>        660              665              670 | 2076 |
| CCG AGT CAC CAG ACA TGG CTG GAA GGA GCC GAG GCT ACT GCG CTG GCC<br>Pro Ser His Gln Thr Trp Leu Glu Gly Ala Glu Ala Thr Ala Leu Ala<br>    675              680              685 | 2124 |
| TGC AGT GCC AGA GGC CGC CCC TCT CCA CGC GTG CGC TGT TCC AGG GAA<br>Cys Ser Ala Arg Gly Arg Pro Ser Pro Arg Val Arg Cys Ser Arg Glu<br>    690              695              700 | 2172 |
| GGT GCA GCC AGG CTG GAG AGG CTA CAG GTG TCC CGA GAG GAT GCG GGG<br>Gly Ala Ala Arg Leu Glu Arg Leu Gln Val Ser Arg Glu Asp Ala Gly<br>705              710              715              720 | 2220 |
| ACC TAC CTG TGT GTG GCT ACC AAC GCG CAT GGC ACG GAT TCA CGG ACC<br>Thr Tyr Leu Cys Val Ala Thr Asn Ala His Gly Thr Asp Ser Arg Thr<br>            725              730              735 | 2268 |
| GTC ACT GTG GGT GTG GAA TAC CGG CCT GTG GTG GCT GAG CTG GCA GCC<br>Val Thr Val Gly Val Glu Tyr Arg Pro Val Val Ala Glu Leu Ala Ala<br>        740              745              750 | 2316 |
| TCG CCC CCA AGC GTG CGG CCT GGC GGA AAC TTC ACT CTG ACC TGC CGT<br>Ser Pro Pro Ser Val Arg Pro Gly Gly Asn Phe Thr Leu Thr Cys Arg<br>    755              760              765 | 2364 |
| GCA GAG GCC TGG CCT CCA GCC CAG ATC AGC TGG CGC GCG CCC CCG GGA<br>Ala Glu Ala Trp Pro Pro Ala Gln Ile Ser Trp Arg Ala Pro Pro Gly<br>    770              775              780 | 2412 |
| GCT CTC AAC CTC GGT CTC TCC AGC AAC AAC AGC ACG CTG AGC GTG GCG<br>Ala Leu Asn Leu Gly Leu Ser Ser Asn Asn Ser Thr Leu Ser Val Ala<br>785              790              795              800 | 2460 |
| GGT GCC ATG GGC AGC CAT GGT GGC GAG TAT GAG TGC GCA GCC ACC AAT<br> | 2508 |

```
                              -continued

Gly  Ala  Met  Gly  Ser  His  Gly  Gly  Glu  Tyr  Glu  Cys  Ala  Ala  Thr  Asn
                    805                      810                     815

GCG  CAT  GGG  CGC  CAC  GCA  CGG  CGC  ATC  ACG  GTG  CGC  GTG  GCC  GGT  CCA      2556
Ala  His  Gly  Arg  His  Ala  Arg  Arg  Ile  Thr  Val  Arg  Val  Ala  Gly  Pro
                    820                      825                     830

TGG  CTG  TGG  GTC  GCT  GTG  GGC  GGT  GCG  GCA  GGG  GGC  GCG  GCG  CTG  CTG      2604
Trp  Leu  Trp  Val  Ala  Val  Gly  Gly  Ala  Ala  Gly  Gly  Ala  Ala  Leu  Leu
                    835                      840                     845

GCC  GCA  GGG  GCC  GGC  CTG  GCC  TTC  TAC  GTG  CAG  TCC  ACC  GCT  TGC  AAG      2652
Ala  Ala  Gly  Ala  Gly  Leu  Ala  Phe  Tyr  Val  Gln  Ser  Thr  Ala  Cys  Lys
          850                      855                     860

AAG  GGA  GAG  TAC  AAC  GTC  CAG  GAG  GCT  GAG  AGC  TCA  GGC  GAG  GCG  GTG      2700
Lys  Gly  Glu  Tyr  Asn  Val  Gln  Glu  Ala  Glu  Ser  Ser  Gly  Glu  Ala  Val
865            870                      875                     880

TGT  CTC  AAT  GGC  GCG  GGC  GGG  ACA  CCG  GGT  GCA  GAA  GGC  GGA  GCA  GAG      2748
Cys  Leu  Asn  Gly  Ala  Gly  Gly  Thr  Pro  Gly  Ala  Glu  Gly  Gly  Ala  Glu
                         885                      890                     895

ACC  CCC  GGC  ACT  GCC  GAG  TCA  CCT  GCA  GAT  GGC  GAG  GTT  TTC  GCC  ATC      2796
Thr  Pro  Gly  Thr  Ala  Glu  Ser  Pro  Ala  Asp  Gly  Glu  Val  Phe  Ala  Ile
                    900                      905                     910

CAG  CTG  ACA  TCT  TCC  TGAGCCTGTA  TCCAGCTCCC  CCAGGGGCCT  CGAAAGCACA             2851
Gln  Leu  Thr  Ser  Ser
                    915

GGGGTGGACG  TATGTATTGT  TCACTCTCTA  TTTATTCAAC  TCCAGGGGCG  TCGTCCCCGT              2911

TTTCTACCCA  TTCCCTTAAT  AAAGTTTTTA  TAGGAGAAAA  AAAAAAAAAA  AAAAAAAAA               2971

AAAAAAAAAA  AAAAAA                                                                 2988
```

( 2 ) INFORMATION FOR SEQ ID NO:2:

( i ) SEQUENCE CHARACTERISTICS:
( A ) LENGTH: 917 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met  Pro  Gly  Pro  Ser  Pro  Gly  Leu  Arg  Arg  Thr  Leu  Leu  Gly  Leu  Trp
 1              5                        10                      15

Ala  Ala  Leu  Gly  Leu  Gly  Ile  Leu  Gly  Ile  Ser  Ala  Val  Ala  Leu  Glu
               20                       25                      30

Pro  Phe  Trp  Ala  Asp  Leu  Gln  Pro  Arg  Val  Ala  Leu  Val  Glu  Arg  Gly
          35                       40                      45

Gly  Ser  Leu  Trp  Leu  Asn  Cys  Ser  Thr  Asn  Cys  Pro  Arg  Pro  Glu  Arg
     50                       55                      60

Gly  Gly  Leu  Glu  Thr  Ser  Leu  Arg  Arg  Asn  Gly  Thr  Gln  Arg  Gly  Leu
65                       70                      75                      80

Arg  Trp  Leu  Ala  Arg  Gln  Leu  Val  Asp  Ile  Arg  Glu  Pro  Glu  Thr  Gln
                    85                       90                      95

Pro  Val  Cys  Phe  Phe  Arg  Cys  Ala  Arg  Arg  Thr  Leu  Gln  Ala  Arg  Gly
               100                      105                     110

Leu  Ile  Arg  Thr  Phe  Gln  Arg  Pro  Asp  Arg  Val  Glu  Leu  Val  Pro  Leu
          115                      120                     125

Pro  Pro  Trp  Gln  Pro  Val  Gly  Glu  Asn  Phe  Thr  Leu  Ser  Cys  Arg  Val
     130                      135                     140

Pro  Gly  Ala  Gly  Pro  Arg  Ala  Ser  Leu  Thr  Leu  Thr  Leu  Leu  Arg  Gly
145                      150                     155                     160

Gly  Gln  Glu  Leu  Ile  Arg  Arg  Ser  Phe  Val  Gly  Glu  Pro  Pro  Arg  Ala
```

-continued

```
                     165                         170                         175
Arg  Gly  Ala  Met  Leu  Thr  Ala  Thr  Val  Leu  Ala  Arg  Arg  Glu  Asp  His
                180                         185                         190
Arg  Ala  Asn  Phe  Ser  Cys  Leu  Ala  Glu  Leu  Asp  Leu  Arg  Pro  His  Gly
                195                         200                         205
Leu  Gly  Leu  Phe  Ala  Asn  Ser  Ser  Ala  Pro  Arg  Gln  Leu  Arg  Thr  Phe
                210                         215                         220
Ala  Met  Pro  Pro  Leu  Ser  Pro  Ser  Leu  Ile  Ala  Pro  Arg  Phe  Leu  Glu
225                           230                         235                         240
Val  Gly  Ser  Glu  Arg  Pro  Val  Thr  Cys  Thr  Leu  Asp  Gly  Leu  Phe  Pro
                     245                         250                         255
Ala  Pro  Glu  Ala  Gly  Val  Tyr  Leu  Ser  Leu  Gly  Asp  Gln  Arg  Leu  His
                260                         265                         270
Pro  Asn  Val  Thr  Leu  Asp  Gly  Glu  Ser  Leu  Val  Ala  Thr  Ala  Thr  Ala
                275                         280                         285
Thr  Ala  Ser  Glu  Glu  Gln  Gly  Thr  Lys  Gln  Leu  Met  Cys  Ile  Val
                290                         295                         300
Thr  Leu  Gly  Gly  Glu  Ser  Arg  Glu  Thr  Gln  Glu  Asn  Leu  Thr  Val  Tyr
305                           310                         315                         320
Ser  Phe  Pro  Ala  Pro  Leu  Leu  Thr  Leu  Ser  Glu  Pro  Glu  Ala  Pro  Glu
                          325                         330                         335
Gly  Lys  Met  Val  Thr  Val  Ser  Cys  Trp  Ala  Gly  Ala  Arg  Ala  Leu  Val
                     340                         345                         350
Thr  Leu  Glu  Gly  Ile  Pro  Ala  Ala  Val  Pro  Gly  Gln  Pro  Ala  Glu  Leu
                355                         360                         365
Gln  Leu  Asn  Val  Thr  Lys  Asn  Asp  Asp  Lys  Arg  Gly  Phe  Phe  Cys  Asp
                370                         375                         380
Ala  Ala  Leu  Asp  Val  Asp  Gly  Glu  Thr  Leu  Arg  Lys  Asn  Gln  Ser  Ser
385                                     390                         395                         400
Glu  Leu  Arg  Val  Leu  Tyr  Ala  Pro  Arg  Leu  Asp  Asp  Leu  Asp  Cys  Pro
                          405                         410                         415
Arg  Ser  Trp  Thr  Trp  Pro  Glu  Gly  Pro  Glu  Gln  Thr  Leu  His  Cys  Glu
                     420                         425                         430
Ala  Arg  Gly  Asn  Pro  Glu  Pro  Ser  Val  His  Cys  Ala  Arg  Pro  Asp  Gly
                435                         440                         445
Gly  Ala  Val  Leu  Ala  Leu  Gly  Leu  Leu  Gly  Pro  Val  Thr  Arg  Ala  Leu
                450                         455                         460
Ala  Gly  Thr  Tyr  Arg  Cys  Thr  Ala  Ile  Asn  Gly  Gln  Gly  Gln  Ala  Val
465                           470                         475                         480
Lys  Asp  Val  Thr  Leu  Thr  Val  Glu  Tyr  Ala  Pro  Ala  Leu  Asp  Ser  Val
                          485                         490                         495
Gly  Cys  Pro  Glu  Arg  Ile  Thr  Trp  Leu  Glu  Gly  Thr  Glu  Ala  Ser  Leu
                     500                         505                         510
Ser  Cys  Val  Ala  His  Gly  Val  Pro  Pro  Pro  Ser  Val  Ser  Cys  Val  Arg
                515                         520                         525
Ser  Gly  Lys  Glu  Glu  Val  Met  Glu  Gly  Pro  Leu  Arg  Val  Ala  Arg  Glu
                530                         535                         540
His  Ala  Gly  Thr  Tyr  Arg  Cys  Glu  Ala  Ile  Asn  Ala  Arg  Gly  Ser  Ala
545                           550                         555                         560
Ala  Lys  Asn  Val  Ala  Val  Thr  Val  Glu  Tyr  Gly  Pro  Ser  Phe  Glu  Glu
                          565                         570                         575
Leu  Gly  Cys  Pro  Ser  Asn  Trp  Thr  Trp  Val  Glu  Gly  Ser  Gly  Lys  Leu
                     580                         585                         590
```

```
Phe  Ser  Cys  Glu  Val  Asp  Gly  Lys  Pro  Glu  Pro  Arg  Val  Glu  Cys  Val
          595                      600                 605

Gly  Ser  Glu  Gly  Ala  Ser  Glu  Gly  Val  Val  Leu  Pro  Leu  Val  Ser  Ser
     610                      615                 620

Asn  Ser  Gly  Ser  Arg  Asn  Ser  Met  Thr  Pro  Gly  Asn  Leu  Ser  Pro  Gly
625                      630                      635                           640

Ile  Tyr  Leu  Cys  Asn  Ala  Thr  Asn  Arg  His  Gly  Ser  Thr  Val  Lys  Thr
                    645                      650                      655

Val  Val  Val  Ser  Ala  Glu  Ser  Pro  Pro  Gln  Met  Asp  Glu  Ser  Ser  Cys
               660                      665                      670

Pro  Ser  His  Gln  Thr  Trp  Leu  Glu  Gly  Ala  Glu  Ala  Thr  Ala  Leu  Ala
          675                      680                      685

Cys  Ser  Ala  Arg  Gly  Arg  Pro  Ser  Pro  Arg  Val  Arg  Cys  Ser  Arg  Glu
          690                     695                      700

Gly  Ala  Ala  Arg  Leu  Glu  Arg  Leu  Gln  Val  Ser  Arg  Glu  Asp  Ala  Gly
705                           710                 715                           720

Thr  Tyr  Leu  Cys  Val  Ala  Thr  Asn  Ala  His  Gly  Thr  Asp  Ser  Arg  Thr
                    725                      730                      735

Val  Thr  Val  Gly  Val  Glu  Tyr  Arg  Pro  Val  Val  Ala  Glu  Leu  Ala  Ala
               740                      745                      750

Ser  Pro  Pro  Ser  Val  Arg  Pro  Gly  Gly  Asn  Phe  Thr  Leu  Thr  Cys  Arg
          755                      760                      765

Ala  Glu  Ala  Trp  Pro  Pro  Ala  Gln  Ile  Ser  Trp  Arg  Ala  Pro  Pro  Gly
     770                      775                      780

Ala  Leu  Asn  Leu  Gly  Leu  Ser  Ser  Asn  Asn  Ser  Thr  Leu  Ser  Val  Ala
785                      790                      795                           800

Gly  Ala  Met  Gly  Ser  His  Gly  Gly  Glu  Tyr  Glu  Cys  Ala  Ala  Thr  Asn
                    805                      810                      815

Ala  His  Gly  Arg  His  Ala  Arg  Arg  Ile  Thr  Val  Arg  Val  Ala  Gly  Pro
               820                      825                      830

Trp  Leu  Trp  Val  Ala  Val  Gly  Gly  Ala  Ala  Gly  Gly  Ala  Ala  Leu  Leu
          835                      840                      845

Ala  Ala  Gly  Ala  Gly  Leu  Ala  Phe  Tyr  Val  Gln  Ser  Thr  Ala  Cys  Lys
     850                      855                      860

Lys  Gly  Glu  Tyr  Asn  Val  Gln  Glu  Ala  Glu  Ser  Ser  Gly  Glu  Ala  Val
865                      870                      875                           880

Cys  Leu  Asn  Gly  Ala  Gly  Gly  Thr  Pro  Gly  Ala  Glu  Gly  Gly  Ala  Glu
                    885                      890                      895

Thr  Pro  Gly  Thr  Ala  Glu  Ser  Pro  Ala  Asp  Gly  Glu  Val  Phe  Ala  Ile
               900                      905                      910

Gln  Leu  Thr  Ser  Ser
          915
```

( 2 ) INFORMATION FOR SEQ ID NO:3:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..315

( x i ) SEQUENCE DESCRIPTION: SEQ ID NO:3:

```
CCG GAT CGG GTA GAG CTA GTG CCT CTG CCT CCT TGG CAG CCT GTA GGT        48
Pro Asp Arg Val Glu Leu Val Pro Leu Pro Pro Trp Gln Pro Val Gly
 1               5                  10                  15

GAG AAC TTC ACC TTG AGC TGC AGG GTC CCG GGG GCA GGA CCC CGA GCG        96
Glu Asn Phe Thr Leu Ser Cys Arg Val Pro Gly Ala Gly Pro Arg Ala
             20                  25                  30

AGC CTC ACA TTG ACC TTG CTG CGA GGC GGA CAG GAG CTG ATT CGC CGA       144
Ser Leu Thr Leu Thr Leu Leu Arg Gly Gly Gln Glu Leu Ile Arg Arg
         35                  40                  45

AGT TTC GTA GGC GAG CCA CCC CGA GCT CGG TGT GCG ATG CTC ACC GCC       192
Ser Phe Val Gly Glu Pro Pro Arg Ala Arg Cys Ala Met Leu Thr Ala
     50                  55                  60

ACG GTC CTG GCG CGC AGA GAG GAT CAC AGG GAC AAT TTC TCA TGC CTC       240
Thr Val Leu Ala Arg Arg Glu Asp His Arg Asp Asn Phe Ser Cys Leu
 65                  70                  75                  80

GCG GAG CTT GAC CTG CGG ACA CAC GGC TTG GGA CTG TTT GCA AAC AGC       288
Ala Glu Leu Asp Leu Arg Thr His Gly Leu Gly Leu Phe Ala Asn Ser
             85                  90                  95

TCA GCC CCC AGA CAG CTC CGC ACG TTT                                   315
Ser Ala Pro Arg Gln Leu Arg Thr Phe
            100                 105
```

( 2 ) INFORMATION FOR SEQ ID NO:4:

( i ) SEQUENCE CHARACTERISTICS:
        ( A ) LENGTH: 1781 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 16..1659

( x i ) SEQUENCE DESCRIPTION: SEQ ID NO:4:

```
CAGCTCTCTG TCAGA ATG GCC ACC ATG GTA CCA TCC GTG TTG TGG CCC AGG       51
               Met Ala Thr Met Val Pro Ser Val Leu Trp Pro Arg
                1               5                  10

GCC TGC TGG ACT CTG CTG GTC TGC TGT CTG CTG ACC CCA GGT GTC CAG        99
Ala Cys Trp Thr Leu Leu Val Cys Cys Leu Leu Thr Pro Gly Val Gln
         15                  20                  25

GGG CAG GAG TTC CTT TTG CGG GTG GAG CCC CAG AAC CCT GTG CTC TCT       147
Gly Gln Glu Phe Leu Leu Arg Val Glu Pro Gln Asn Pro Val Leu Ser
     30                  35                  40

GCT GGA GGG TCC CTG TTT GTG AAC TGC AGT ACT GAT TGT CCC AGC TCT       195
Ala Gly Gly Ser Leu Phe Val Asn Cys Ser Thr Asp Cys Pro Ser Ser
 45                  50                  55                  60

GAG AAA ATC GCC TTG GAG ACG TCC CTA TCA AAG GAG CTG GTG GCC AGT       243
Glu Lys Ile Ala Leu Glu Thr Ser Leu Ser Lys Glu Leu Val Ala Ser
             65                  70                  75

GGC ATG GGC TGG GCA GCC TTC AAT CTC AGC AAC GTG ACT GGC AAC AGT       291
Gly Met Gly Trp Ala Ala Phe Asn Leu Ser Asn Val Thr Gly Asn Ser
                 80                  85                  90

CGG ATC CTC TGC TCA GTG TAC TGC AAT GGC TCC CAG ATA ACA GGC TCC       339
Arg Ile Leu Cys Ser Val Tyr Cys Asn Gly Ser Gln Ile Thr Gly Ser
         95                 100                 105

TCT AAC ATC ACC GTG TAC GGG CTC CCG GAG CGT GTG GAG CTG GCA CCC       387
Ser Asn Ile Thr Val Tyr Gly Leu Pro Glu Arg Val Glu Leu Ala Pro
    110                 115                 120

CTG CCT CCT TGG CAG CCG GTG GGC CAG AAC TTC ACC CTG CGC TGC CAA       435
Leu Pro Pro Trp Gln Pro Val Gly Gln Asn Phe Thr Leu Arg Cys Gln
125                 130                 135                 140
```

| | | | | | | | | | | | | | | | | |
|---|---|---|---|---|---|---|---|---|---|---|---|---|---|---|---|---|
| GTG | GAG | GGT | GGG | TCG | CCC | CGG | ACC | AGC | CTC | ACG | GTG | GTG | CTG | CTT | CGC | 483 |
| Val | Glu | Gly | Gly | Ser | Pro | Arg | Thr | Ser | Leu | Thr | Val | Val | Leu | Leu | Arg | |
| | | | | 145 | | | | | 150 | | | | | 155 | | |
| TGG | GAG | GAG | GAG | CTG | AGC | CGG | CAG | CCC | GCA | GTG | GAG | GAG | CCA | GCG | GAG | 531 |
| Trp | Glu | Glu | Glu | Leu | Ser | Arg | Gln | Pro | Ala | Val | Glu | Glu | Pro | Ala | Glu | |
| | | | 160 | | | | | 165 | | | | | 170 | | | |
| GTC | ACT | GCC | ACT | GTG | CTG | GCC | AGC | AGA | GAC | GAC | CAC | GGA | GCC | CCT | TTC | 579 |
| Val | Thr | Ala | Thr | Val | Leu | Ala | Ser | Arg | Asp | Asp | His | Gly | Ala | Pro | Phe | |
| | | | 175 | | | | | 180 | | | | | 185 | | | |
| TCA | TGC | CGC | ACA | GAA | CTG | GAC | ATG | CAG | CCC | CAG | GGG | CTG | GGA | CTG | TTC | 627 |
| Ser | Cys | Arg | Thr | Glu | Leu | Asp | Met | Gln | Pro | Gln | Gly | Leu | Gly | Leu | Phe | |
| | | | 190 | | | | | 195 | | | | | 200 | | | |
| GTG | AAC | ACC | TCA | GCC | CCC | CGC | CAG | CTC | CGA | ACC | TTT | GTC | CTG | CCC | GTG | 675 |
| Val | Asn | Thr | Ser | Ala | Pro | Arg | Gln | Leu | Arg | Thr | Phe | Val | Leu | Pro | Val | |
| 205 | | | | | 210 | | | | | 215 | | | | | 220 | |
| ACC | CCC | CCG | CGC | CTC | GTG | GCC | CCC | CGG | TTC | TTG | GAG | GTG | GAA | ACG | TCG | 723 |
| Thr | Pro | Pro | Arg | Leu | Val | Ala | Pro | Arg | Phe | Leu | Glu | Val | Glu | Thr | Ser | |
| | | | | 225 | | | | | 230 | | | | | 235 | | |
| TGG | CCG | GTG | GAC | TGC | ACC | CTA | GAC | GGG | CTT | TTT | CCA | GCC | TCA | GAG | GCC | 771 |
| Trp | Pro | Val | Asp | Cys | Thr | Leu | Asp | Gly | Leu | Phe | Pro | Ala | Ser | Glu | Ala | |
| | | | 240 | | | | | 245 | | | | | 250 | | | |
| CAG | GTC | TAC | CTG | GCG | CTG | GGG | GAC | CAG | ATG | CTG | AAT | GCG | ACA | GTC | ATG | 819 |
| Gln | Val | Tyr | Leu | Ala | Leu | Gly | Asp | Gln | Met | Leu | Asn | Ala | Thr | Val | Met | |
| | | | 255 | | | | | 260 | | | | | 265 | | | |
| AAC | CAC | GGG | GAC | ACG | CTA | ACG | GCC | ACA | GCC | ACA | GCC | ACG | GCG | CGC | GCG | 867 |
| Asn | His | Gly | Asp | Thr | Leu | Thr | Ala | Thr | Ala | Thr | Ala | Thr | Ala | Arg | Ala | |
| | | | 270 | | | | | 275 | | | | | 280 | | | |
| GAT | CAG | GAG | GGT | GCC | CGG | GAG | ATC | GTC | TGC | AAC | GTG | ACC | CTA | GGG | GGC | 915 |
| Asp | Gln | Glu | Gly | Ala | Arg | Glu | Ile | Val | Cys | Asn | Val | Thr | Leu | Gly | Gly | |
| 285 | | | | | 290 | | | | | 295 | | | | | 300 | |
| GAG | AGA | CGG | GAG | GCC | CGG | GAG | AAC | TTG | ACG | GTC | TTT | AGC | TTC | CTA | GGA | 963 |
| Glu | Arg | Arg | Glu | Ala | Arg | Glu | Asn | Leu | Thr | Val | Phe | Ser | Phe | Leu | Gly | |
| | | | | 305 | | | | | 310 | | | | | 315 | | |
| CCC | ATT | GTG | AAC | CTC | AGC | GAG | CCC | ACC | GCC | CAT | GAG | GGG | TCC | ACA | GTG | 1011 |
| Pro | Ile | Val | Asn | Leu | Ser | Glu | Pro | Thr | Ala | His | Glu | Gly | Ser | Thr | Val | |
| | | | 320 | | | | | 325 | | | | | 330 | | | |
| ACC | GTG | AGT | TGC | ATG | GCT | GGG | GCT | CGA | GTC | CAG | GTC | ACG | CTG | GAC | GGA | 1059 |
| Thr | Val | Ser | Cys | Met | Ala | Gly | Ala | Arg | Val | Gln | Val | Thr | Leu | Asp | Gly | |
| | | | 335 | | | | | 340 | | | | | 345 | | | |
| GTT | CCG | GCC | GCG | GCC | CCG | GGG | CAG | ACA | GCT | CAA | CTT | CAG | CTA | AAT | GCT | 1107 |
| Val | Pro | Ala | Ala | Ala | Pro | Gly | Gln | Thr | Ala | Gln | Leu | Gln | Leu | Asn | Ala | |
| | | | 350 | | | | | 355 | | | | | 360 | | | |
| ACC | GAG | AGT | GAC | GAC | GGA | CGC | AGC | TTC | TTC | TGC | AGT | GCC | ACT | CTC | GAG | 1155 |
| Thr | Glu | Ser | Asp | Asp | Gly | Arg | Ser | Phe | Phe | Cys | Ser | Ala | Thr | Leu | Glu | |
| 365 | | | | | 370 | | | | | 375 | | | | | 380 | |
| GTG | GAC | GGC | GAG | TTC | TTG | CAC | AGG | AAC | AGT | AGC | GTC | CAG | CTG | CGA | GTC | 1203 |
| Val | Asp | Gly | Glu | Phe | Leu | His | Arg | Asn | Ser | Ser | Val | Gln | Leu | Arg | Val | |
| | | | | 385 | | | | | 390 | | | | | 395 | | |
| CTG | TAT | GGT | CCC | AAA | ATT | GAC | CGA | GCC | ACA | TGC | CCC | CAG | CAC | TTG | AAA | 1251 |
| Leu | Tyr | Gly | Pro | Lys | Ile | Asp | Arg | Ala | Thr | Cys | Pro | Gln | His | Leu | Lys | |
| | | | 400 | | | | | 405 | | | | | 410 | | | |
| TGG | AAA | GAT | AAA | ACG | AGA | CAC | GTC | CTG | CAG | TGC | CAA | GCC | AGG | GGC | AAC | 1299 |
| Trp | Lys | Asp | Lys | Thr | Arg | His | Val | Leu | Gln | Cys | Gln | Ala | Arg | Gly | Asn | |
| | | | 415 | | | | | 420 | | | | | 425 | | | |
| CCG | TAC | CCC | GAG | CTG | CGG | TGT | TTG | AAG | GAA | GGC | TCC | AGC | CGG | GAG | GTG | 1347 |
| Pro | Tyr | Pro | Glu | Leu | Arg | Cys | Leu | Lys | Glu | Gly | Ser | Ser | Arg | Glu | Val | |
| | | | 430 | | | | | 435 | | | | | 440 | | | |
| CCG | GTG | GGG | ATC | CCG | TTC | TTC | GTC | AAC | GTA | ACA | CAT | AAT | GGT | ACT | TAT | 1395 |
| Pro | Val | Gly | Ile | Pro | Phe | Phe | Val | Asn | Val | Thr | His | Asn | Gly | Thr | Tyr | |
| 445 | | | | | 450 | | | | | 455 | | | | | 460 | |

```
CAG TGC CAA GCG TCC AGC TCA CGA GGC AAA TAC ACC CTG GTC GTG GTG       1443
Gln Cys Gln Ala Ser Ser Ser Arg Gly Lys Tyr Thr Leu Val Val Val
                465                 470                 475

ATG GAC ATT GAG GCT GGG AGC TCC CAC TTT GTC CCC GTC TTC GTG GCG       1491
Met Asp Ile Glu Ala Gly Ser Ser His Phe Val Pro Val Phe Val Ala
            480                 485                 490

GTG TTA CTG ACC CTG GGC GTG GTG ACT ATC GTA CTG GCC TTA ATG TAC       1539
Val Leu Leu Thr Leu Gly Val Val Thr Ile Val Leu Ala Leu Met Tyr
        495                 500                 505

GTC TTC AGG GAG CAC CAA CGG AGC GGC AGT TAC CAT GTT AGG GAG GAG       1587
Val Phe Arg Glu His Gln Arg Ser Gly Ser Tyr His Val Arg Glu Glu
    510                 515                 520

AGC ACC TAT CTG CCC CTC ACG TCT ATG CAG CCG ACA GAA GCA ATG GGG       1635
Ser Thr Tyr Leu Pro Leu Thr Ser Met Gln Pro Thr Glu Ala Met Gly
525                 530                 535                 540

GAA GAA CCG TCC AGA GCT GAG TGACGCTGGG ATCCGGATC AAAGTTGGCG           1686
Glu Glu Pro Ser Arg Ala Glu
                545

GGGGCTTGGC TGTGCCCTCA GATTCCGCAC CAATAAAGCC TTCAAACTCC CAAAAAAAA     1746
AAAAAAAAAA AAAAAAAAAA AAAAAAAAAA AAAAA                               1781
```

( 2 ) INFORMATION FOR SEQ ID NO:5:

( i ) SEQUENCE CHARACTERISTICS:
        ( A ) LENGTH: 4900 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CCGAACGCTC CTCGGCCTCT GGTCTNCTCT GGNCCTGGGG ATCCTAGGCA TCTCAGGTAA      60
GAAGAGCCCG CCCGTGGAGC NAGGTGGATA AGGCGGGGGC GGAATTGAAG GACCAGAGAG     120
GGCGGCCCGG GTGTCCCCCT CCAGGCTCCG CCCTCTTCTA GCTTCCCACG CTTCTGTCAC     180
CACCTGGAGN TCGGGCTTC TCCCCGTCCT TCCTCCACCC CAACACACCT CAATCTTTCA      240
GANCTGAACC CAGCACCTTT TCTGGANTNG GGGNNTTGCA CCTAACCTGT CTCAGGAGAN     300
ACTGTGGCTC TCCTGTCCTC TCCTGCTCTG TNATGCCCTA TGGTTCACAG ACTGGCATCA     360
TCCCTATTCA TGATCCTCAA AGACNCCATC TCCTCAACTG TCATAACTCA GAGCTCTATT     420
CCCCCTCCAC CTGGAGCCCT GGAAACCGGC TTTCTAGGGC TTTTCTCCGC GGTTCTTTCC     480
CGGAGTTCAG CGTTGTGGCT TTTTGTCCAA GTTACTCAAG TTTGGGGACA ATCTCCTTTA     540
AGCCTTTGAC TCAGTCTCAT TTCCACTTTG CTTTGCCCC AAGCCTCTGT GTCTCTCCCC      600
CATTTCCTGA CGATCTGTCA GAGTCTTAAG AGTGATTTGG TTCCCCATCC CCCTCCAAC      660
TGGAGTCTCC TCCTCACTAT TGATGTGTGC ATCTGAGACC CCCATCCCCG CACCGAGTTT     720
CCCCATCTCT GTCAGTAAAG AGCAAGGCTT CCAGAGACAA CCCTCTAATA GCGCGTCAGT     780
CCCGAATCTT GAGTGGGATG CGGGACTCCC GTGCTATTTC TTGGCGGAGG TCTTTCCTGG     840
TCCTTATGGA CACCCCTGGT TTGGATATG GGGCCGCTA AGATTTCAGA GATGGGGTCC       900
CTAGGCTGAG NCCGCGTTTT CCCGGGCAGC GGTCGCGCTA GAACCTTTCT GGGCGGACCT     960
TCAGCCCCGC GTGGCGCTCG TGGAGCGCGG GGCTCGCTG TGGCTCAACT GCAGCACTAA     1020
CTGTCCGAGG CCGGAGCGCG GTGGCCTGGA GACCTCGCTA CGCCGAAACG GGACCCAGAG    1080
GGGTCTGNAC TGNCTGGCTC GACAGCTGGT GGACATCCGA GANCCTGAAA CCCAGCCGGT    1140
```

| | | | | | |
|---|---|---|---|---|---|
| CTGCTTCTTC | CNCTGCGCGC | GCCGCACACT | CCAAGCGCGT | GGGCTCATCC | GAACTTTCCG | 1200
| TGAGTTCAGG | GTGGGCACNC | CCCTTGGGTC | TCTGGACCTC | CCCCTCAAGC | TCCTCCCACC | 1260
| CGCCCTCTGA | TCCTCCTGCT | TGTTCTGAAA | GTACTACAGC | TGGCTAGAGC | GGAGTTTTTG | 1320
| GTCCCTTGCA | GAGCGACCGG | ATCGGGTAGA | GCTAGTGCCT | CTGCCTCCTT | GGCAGCCTGT | 1380
| AGGTGAGAAC | TTCACCTTGA | GCTGCAGGGT | CCCGGGGGCA | GGACCCCGAG | CGAGCCTCAC | 1440
| ATTGACCTTG | CTGCGAGGCG | GCCAGGAGCT | GATTCGCCGA | AGTTTCGTAG | GCGAGCCACC | 1500
| CCGAGCTCGG | GGTGCGATGC | TCACCGCCAC | GGTCCTGGCG | CGCAGAGAGG | ATCACAGGGC | 1560
| CAATTTCTCA | TGCCTCGCGG | AGCTTGACCT | GCGNCCACAC | GGCTTGGGAC | TGTTTGCANA | 1620
| CAGCTCAGCC | CCCAGACAGC | TCCGCACGTT | TGGTGAGTGT | GGACCCTAAC | TGACAGATTT | 1680
| TAAGAAGTTT | AGGGCAGCCA | GGCGTGGTGG | CATGGTGTCG | TAGGCCCTAA | GTCCCAGCCC | 1740
| AAGCAGANCT | AAGNCGGATC | TCTTGTGAAT | TAAAAGTCTA | GCTCGTCTAC | ATAACGAGGN | 1800
| CTGCATAGTT | AAATCCCCCA | AAAGTCTAAG | CAGCTAGCCC | TTACTTCCAA | CACAAGTACT | 1860
| AGCTTAAGTA | CTTTCTCCTG | TGAGCTTTTT | CCTTTATGTA | TTTACTCGTT | GAGAGAAAAA | 1920
| GAGAGTGTGT | GTACGTGCCT | TTATGCACAT | GCCGCAGTGC | TTGTATGGAA | GTTAAAGAAT | 1980
| AAGGAGGCGT | TCTGCCCTTC | CATCCTGTGG | GTCCTAGGGG | TGGTATTAGC | TCCTCAGGCT | 2040
| TTGTTAGTNA | CAAGCGCCTA | GGCTTGGGGA | GCCATCTCGC | CCGCTCCTCT | GTATCTTTAG | 2100
| GGTGAAACCA | GACAATGCAT | GCAAATTGGT | TGATCAACAC | TGAATGTTTA | GTTCGTAAAT | 2160
| TCAAGCTCTG | TTCTTTGTCT | TCCTCAGCCA | TGCCTCCACT | TTCCCCCGAG | CCTTATTGCC | 2220
| CCACGATTCT | TAGAAGTGGG | CTCAGAAAGG | CCGGTGACKT | GCACTTTGGA | TGGACTGTTT | 2280
| CCTGCCCCAG | AAGCCGGGGT | TTACTTCTCT | CTGGGAGATC | AGAGGCTTCA | TCCTAATGTG | 2340
| ACCCTCGACG | GGGAGAGCCT | TGTGGCCACT | GCCACAGCTA | CAGCAAGTGA | AGAACAGGAA | 2400
| GGCACCAAAC | AGCTGATGTG | CATCGTGACC | CTCGGGGCG | AAAGCAGGGA | GACCCAGGAA | 2460
| AACCTGACTG | TCTACAGTAA | GGGGAATCCA | ACAAGACCTT | CAATAGCTCA | GACTGGGGCT | 2520
| GGGGCTGGGT | CTGGGTCTGG | GGCCAGAGTC | TCACAAAGGC | GGAGCCTATA | AAGTGGGCGG | 2580
| GACCTCCACA | CCAGAACAAG | CCGGGCGGGA | GAGTTCCAGG | GCAGGAGCAG | ATAGAAGTTG | 2640
| GAAATTAATA | GATTGGGTTG | AGTTCCCTGA | GTGGGAGTG | AACCCCACCC | AATTCTCTGT | 2700
| CCCCAGGCTT | CCCGGCTCCT | CTTCTGACTT | TAAGTGAGCC | AGAAGCCCCC | GAGGGAAAGA | 2760
| TGGTGACCGT | AAGCTGCTGG | GCAGGGGCCC | GAGCCCTTGT | CACCTTGGAG | GGAATTCCAA | 2820
| GGACCCTCTT | ACCGGCCCCA | TCTTTAACCT | TATCGTATCC | CCTCTGCCTC | ATGCCCGCAG | 2880
| ACGCACCTCG | GCTGGATGAC | TTGGACTGTC | CCAGGAGCTG | GACGTGGCCA | GAGGGTCCAG | 2940
| AGCAGACCCT | CCACTGCGAG | GCCCGTGGAA | ACCCTGAGCC | CTCCGTGCAC | TGTGCAAGGC | 3000
| CTGACGGTGG | GGCGGTGCTA | GCGCTGGGCC | TGTTGGGTCC | AGTGACCCGT | GCCCTCGCGG | 3060
| GCACTTACCG | ATGTACAGCA | ATCAATGGGC | AAGGCCAGGC | GGTCAAGGAT | GTGACCCTGA | 3120
| CTGTGGAATG | TGAGTAGGGG | GAGGTGGGCA | TGCTTATCCC | TTTAAGGTCA | CGGAGTGTAC | 3180
| TGGGAGACTG | GCTATACGGA | AAGGAAAGAA | GCCTAGGTTC | AGCAGGGATT | GGGAAAACAC | 3240
| TGAAGGAAAG | TGGTGTGGTG | TTTACAAACT | TAACGGTGGT | AACTGGGCAC | GGTCTGGCAA | 3300
| AAACAGACAG | CCAAGAGAGT | GTGCCTGGGA | AGCTGCAATG | GGGCTTTGT | GGAATTGGT | 3360
| CAACAGCACC | CTGAGATCTC | AGGAAGGGG | CCTGAAGTTA | TCTCCAGAAC | CCATGTGAAG | 3420
| GCAGGAAGAG | AGAACGCCCA | CCTTTTCCTG | CTCCCCCCAA | CCCCCCCCCA | CATATCACAC | 3480
| GGAGTATATA | AATAAATAAA | ATGGCTCCTG | CCGGAGGGAG | TGAGAAGCTG | TCTCCTGCAG | 3540

-continued

| | | | | | |
|---|---|---|---|---|---|
| GCTCAGAGCA | GTGGTAGTGC | ATGCCTTTAA | TCCCAGCACT | CGGTAGGCAA | AGGCAGGCAG | 3600 |
| ATCTCTGTGA | ATGTGGGGCC | AGCCTGGTCT | GTACAGAGAA | ATCCTGTCTC | AAAACAAACC | 3660 |
| AGCAAAGAAA | CAAAACCAAA | ATCAATTCCA | GATGCCCCAG | CGCTGGACAG | TGTAGGCTGC | 3720 |
| CCANGACGTA | TTACTTGNCT | GGAGGGGACA | GAGGCATCGC | TTAGCTGTGT | GGCACACGGG | 3780 |
| GTCCCACCAC | CTAGCGTGAG | CTGTGTGCGC | TCTGGAAAGG | AGGAAGTCAT | GGAAGGGCCC | 3840 |
| CTGCGTGTGG | CCCGGGAGCA | CGCTGGCACT | TACCGATGCG | AAGCCATCAA | CGCCAGGGGA | 3900 |
| TCAGCGGNCA | AAAATGTGGC | TGTCACGGTG | GAATGTGAGT | AGGGGTGGCT | ACGGAAATGT | 3960 |
| CCACACCTGC | GTCCTCTGTC | CTCAGTGTGA | ACTCCTATTT | CCCTGCTTCC | TAGATGGTCC | 4020 |
| CAGTTNTGAG | GAGTTGGGCT | GCCCCAGCAA | CTGGACTTGG | GTAGAAGGAT | CTGGAAAACT | 4080 |
| GTTTTCCTGT | GAAGTTGATG | GGAAGCCGGA | ACCACGCGTG | GAGTGCGTGG | GCTCGGAGGG | 4140 |
| TGCAAGCGAA | GGGGTAGTGT | TGCCCCTGGT | GTCCTCGAAC | TCTGGTTCCA | GAAACTCTAT | 4200 |
| GACTCCTGGT | AACCTGTCAC | CGGGTATTTA | CCTCTGCAAC | GCCACCAACC | GGCATGGCTC | 4260 |
| CACAGTCAAA | ACAGTCGTCG | TGAGCGCGGA | ATGTGAGCAG | GGGCCCAGGT | GGGCGGAGAG | 4320 |
| TACCGGGTGT | CCCAGGATCT | TTTCTTTCCC | TGATGCCCCT | CCTTATGGTG | GCTGATCTGC | 4380 |
| AGCACCGCCA | CAGATGGATG | AATCCAGTTG | CCCGAGTCAC | CAGACATGGC | TGGAAGGAGC | 4440 |
| CGAGGCTACT | GCGCTGGCCT | GCAGTGACAG | GGGNCGCCCC | TCTCCACGCG | TGCGCTGTTC | 4500 |
| CAGGGAAGGT | GCAGCCAGGC | TGGAGAGGCT | ACAGGTGTCC | CGAGAGGATG | CGGGGACCTA | 4560 |
| CCTGTGTGTG | GCTACCAACG | CGCATGGCAC | GGATTCACGG | ACCGTCACTG | TGGGTGTGGA | 4620 |
| ATGTGAGTGA | GGACAGCGCT | GAATGAAGAC | GACTCAGACC | GCCAGAAAAG | TGCCTTGAGG | 4680 |
| CCTGGGATGT | ATGATCCAGT | GGGTAGAGTG | CTCAATTAGC | ACTCACTAAA | ATGTATATTC | 4740 |
| TATTCCTAAT | ACTCTTTAAT | TTTANCCTTT | GGGAGGCAGA | GACAGGCAGA | TCTCTGTTCC | 4800 |
| GGGATAACCT | GCTCTCTGTC | TAGGACAGCT | TGGTCTACAG | AGGGGNTACA | GGCCCCCCCT | 4860 |
| CCCAAGATTG | NATAGCAACC | CTCTGGCTCC | CTGTCTCTCT | | | 4900 |

( 2 ) INFORMATION FOR SEQ ID NO:6:

( i ) SEQUENCE CHARACTERISTICS:
        ( A ) LENGTH: 1295 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---|
| NGAATTCCGG | CGGATCGGGT | AGAGCTAGTG | CCTCTGCCTC | CTTGGCAGCC | TGTAGGTGAG | 60 |
| AACTTCACCT | TGAGCTGCAG | GGTCCCGGGG | GCAGGACCCC | GAGCGAGCCT | CACATTGACC | 120 |
| TTGCTGCGAG | GCGGCCAGGA | GCTGATTCGC | CGAAGTTTCG | TAGGCGAGCC | ACCCCGAGCT | 180 |
| CGGGGTGCGA | TGCTCACCGC | CACGGTCCTG | GCGCGCAGAG | AGGATCACAG | GGCCAATTTC | 240 |
| TCATGCCTCG | CGGAGCTTGA | CCTGCGGCCA | CACGGCTTGG | GACTGTTTGC | AAACAGCTCA | 300 |
| GCCCCCAGAC | AGCTCCGCAC | GTTTGCCATG | CCTCCACTTT | CCCCGAGCCT | TATTGCCCCA | 360 |
| CGATTCTTAG | AAGTGGGCTC | AGAAAGGCCG | GTGACTTGCA | CTTTGGATGG | ACTGTTTCCT | 420 |
| GCCCCAGAAG | CCGGGGTTTA | CCTCTCTCTG | GGAGATCAGA | GGCTTCATCC | TAATGTGACC | 480 |
| CTCGACGGGG | AGAGCCTTGT | GGCCACTGCC | ACAGCTACAG | CAAGTGAAGA | ACAGGAAGGC | 540 |
| ACCAAACAGC | TGATGTGCAT | CGTGACCCTC | GGGGCGAAA | GCAGGGAGAC | CCAGGAAAAC | 600 |
| CTGACTGTCT | ACAGCTTCCC | GGCTCCTCTT | CTGACTTTAA | GTGAGCCAGA | AGCCCCCGAG | 660 |

-continued

| | | | | | |
|---|---|---|---|---|---|
| GGAAAGATGG | TGACCGTAAG | CTGCTGGGCA | GGGGCCCGAG | CCCTTGTCAC | CTTGGAGGGA | 720 |
| ATTCCAAGGA | CCCTCTTACC | GGCCCCATCT | TTAACCTTAT | CGTATCCCCT | CTGCCTCATG | 780 |
| CCCGCAGACG | CACCTCGGCT | GGATGACTTG | GACTGTCCCA | GGAGCTGGAC | GTGGCCAGAG | 840 |
| GGTCCAGAGC | AGACCCTCCA | CTGCGAGGCC | CGTGGAAACC | CTGAGCCCTC | CGTGCACTGT | 900 |
| GCAAGGCCTG | ACGGTGGGC | GGTGCTAGCG | CTGGGCCTGT | TGGGTCCAGT | GACCCGTGCC | 960 |
| CTCGCGGGCA | CTTACCGATG | TACAGCAATC | AATGGGCAAG | GCCAGGCGGT | CAAGGATGTG | 1020 |
| ACCCTGACTG | TGGAATATGC | CCCAGCGCTG | GACAGTGTAG | GCTGCCCAGA | ACGTATTACT | 1080 |
| TGGCTGGAGG | GGACAGAGGC | ATCGCTTAGC | TGTGTGGCAC | ACGGGGTCCC | ACCACCTAGC | 1140 |
| GTGAGCTGTG | TGCGCTCTGG | AAAGGAGGAA | GTCATGGAAG | GGCCCCTGCG | TTTTGGCCGG | 1200 |
| GAGCACGCTG | GCACTTACCG | ATGCGAAGCC | ATCAACGCCA | GGGGATCAGC | GGCCAAAAAT | 1260 |
| GTGGCTGTCA | CGGTGGAATA | TGGTCCCCGG | AATTC | | | 1295 |

(2) INFORMATION FOR SEQ ID NO:7:

(i) SEQUENCE CHARACTERISTICS:
        (A) LENGTH: 2214 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

| | | | | | |
|---|---|---|---|---|---|
| CGAATCTTGA | GTGGGATGCG | GGACTCCCGT | GCTATTTCTT | GGCGGAGGTC | TTTCCTGGTC | 60 |
| CTTATGGACA | CCCCTGGTTT | GGGATATGGG | GGCCGCTAAG | ATTTCAGAGA | TGGGGTCCCT | 120 |
| AGGCTGAGCC | CGCGTTTTCC | CGGGCAGCGG | TCGCGCTAGA | ACCTTTCTGG | GCGGACCTTC | 180 |
| AGCCCCGCGT | GGCGCTCGTG | GAGCGCGGGG | GCTCGCTGTG | GCTCAACTGC | AGCACTAACT | 240 |
| GTCCGAGGCC | GGAGCGCGGT | GGYCTGGAGA | CCTCGCTACG | CCGAAACGGG | ACCCAGAGGG | 300 |
| GTCTGCGCTG | GCTGGCTCGA | CAGMTGGTGG | ACATCCGAGA | GCCTGAAACC | CAGTCGGTCT | 360 |
| GCTTCTTCCG | CTGGGCGCGC | CGCACACTCC | AAGNGAGTGG | GCTCATCCGA | ACTTTCCAGC | 420 |
| GACCGGATCG | GGTAGAGCTA | GTGCCTCTGN | CTCCTTGGCA | GCCTGTAGGT | GAGAACTTCA | 480 |
| CCTTGAGCTG | CAGGGTCCCG | GGGCAGGAC | CCCGAGCGAG | CCTCACATTG | ACCTTGCTGC | 540 |
| GAGGCGGCCA | GGAGCTGATT | CGCCGAAGTT | TCGTAGGCGA | GCCACCCCGA | GCTCGGGGTG | 600 |
| CGATGCTCAC | CGCCACGGTC | CTGGCGCGCA | GAGAGGATCA | CAGGGCCAAT | TTCTCATGCC | 660 |
| TCGCGGAGCT | TGACCTGCGG | ACACACGGCT | TGGGACTGTT | TGCAAACAGC | TCAGCCCCCA | 720 |
| GACAGCTCCG | CACGTTTGGC | ATGCCTCCAC | TTTCCCCGAG | CCTTATTGNC | CCACGATTCT | 780 |
| TAGAAGTGGG | CTCAGAAAGG | CCGGTGACTT | GCACTTTGGA | TGGACTGTTT | CCTGCCCCAG | 840 |
| AAGCCGGGGT | TTACCTCTCT | CTGGGAGATC | AGAGGCTTCA | TCCTAATGTG | ACCCTCGACG | 900 |
| GGGAGAGCCT | TGTGGCCACT | GNCACAGMTA | CAGCAAGTGA | AGAACAGGAA | GGCACCAAAC | 960 |
| AGCTGATGTG | CATCGTGACC | CTCGGGGGCG | AAAGCAGGGA | GACCCAGGAA | AACCTGACTG | 1020 |
| TCTACAGCTT | CCCGGCTCCT | CTTCTGACTT | TAAGTGAGCC | AGAAGCCCCC | GAGGGAAAGA | 1080 |
| TGGTGACCGT | AAGCTGCTGG | GCAGGGCCC | GAGCCCTTGT | CACCTTGGAG | GGAATTCCAG | 1140 |
| CTGCGGTCCC | TGGCAGCCC | GCTGAGCTCC | AGTTAAATGT | CACAAAGAAT | GACGACAAGC | 1200 |
| GGGGCTTCTT | CTGCGACGCT | GCCCTCGATG | TGGACGGGGA | AACTCTGAGA | AAGAACCAGA | 1260 |
| GCTCTGAGCT | TCGTGTTCTG | TACGCACCTC | GGCTGGATGA | CTTGGACTGT | CCCAGGAGCT | 1320 |

```
GGACGTGGCC  AGAGGGTCCA  GAGCAGACCC  TCCACTGCGA  GGCCCGTGGA  AACCCTGAGC    1380
CCTCCGTGCA  CTGTGCAAGG  CCTGACGGTG  GGGCGGTGCT  AGCGCTGGGC  CTGTTGGGTC    1440
CAGTGACCCG  TGCCCTCGCG  GGAACTTACC  GATGTACAGC  AATCAATGGG  CAAGGCCAGG    1500
CGGTCAAGGA  TGTGACCCTG  ACTGTGGAAT  ATGCCCAGC   GCTGGACAGT  GTAGGCTGCC    1560
CAGAACGTAT  TACTTGGCTG  GAGGGGACAG  AGGCATCGCT  TAGCTGTGTG  GCACACGGGG    1620
TCCCACCACC  TAGCGTGAGC  TGTGTGCGCT  CTGGAAAGGA  GGAAGTCATG  GAAGGGCCCC    1680
TGCGTGTGGC  CCGGGAGCAC  GCTGGCACTT  ACCGATGCGA  AGCCATCAAC  GNCAGGGAT     1740
CAGCGGWCAA  AAATGTGGCT  GTCACGGTGG  AATATGGTCC  CAGTTGGAG   GAGTTGGGCT    1800
GCCCCAG Y AA  CTGGACTTGG  GTAGAAGGAT  CTGGAAAACT  GTTTCCTGT  GAAGTTGATG   1860
GGAAGCCGGA  ACCACGCGTG  GAGTGCGTGG  GCTCGGAGGG  TGCAAGCGAA  GGGGTAGTGT    1920
TGCCCCTGGT  GTCCTCGAAC  TCTGGTTCCA  GAAACTCTAT  GACTCCTGGT  AACCTGTCAC    1980
CGGGTATTTA  CCTCTGCAAC  GCCACCAACC  GGMATGGNTC  CACAGTCAAA  ACAGTCGTCG    2040
TGAGCGCGGA  ATCACCGCCA  CAGATGGATG  AATCCAGTTG  CCCGAGTCAC  CAGACATGGN    2100
TGGAAGGAGC  CGAGGNTACT  GCGCTGGCCT  GCAGTGCCAG  AGGNCGCCC   TCTCCACGCG    2160
TGCGCTGTTC  CAGGGAAGGT  GCAGMCAGGC  TGGAGAGGNT  ACAGGTGTCC  CGAG          2214
```

( 2 ) INFORMATION FOR SEQ ID NO:8:

( i ) SEQUENCE CHARACTERISTICS:
( A ) LENGTH: 5077 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

```
CCGAACGCTC  CTCGGCCTCT  GGTCTNCTCT  GGNCCTGGGG  ATCCTAGGCA  TCTCAGGTAA    60
GAAGAGCCCG  CCCGTGGAGC  NAGGTGGATA  AGGCGGGGGC  GGAATTGAAG  GACCAGAGAG    120
GGCGGCCCGG  GTGTCCCCCT  CCAGGCTCCG  CCCTCTTCTA  GCTTCCCACG  CTTCTGTCAC    180
CACCTGGAGN  TCGGGGCTTC  TCCCCGTCCT  TCCTCCACCC  CAACACACCT  CAATCTTTCA    240
GANCTGAACC  CAGCACCTTT  TCTGGANTNG  GGGNNTTGCA  CCTAACCTGT  CTCAGGAGAN    300
ACTGTGGCTC  TCCTGTCCTC  TCCTGCTCTG  TNATGCCCTA  TGGTTCACAG  ACTGGCATCA    360
TCCCTATTCA  TGATCCTCAA  AGACNCCATC  TCCTCAACTG  TCATAACTCA  GAGCTCTATT    420
CCCCCTCCAC  CTGGAGCCCT  GGAAACCGGC  TTTCTAGGGC  TTTTCTCCGC  GGTTCTTTCC    480
CGGAGTTCAG  CGTTGTGGCT  TTTTGTCCAA  GTTACTCAAG  TTTGGGGACA  ATCTCCTTTA    540
AGCCTTTGAC  TCAGTCTCAT  TTCCACTTTG  CTTTTGCCCC  AAGCCTCTGT  GTCTCTCCCC    600
CATTTCCTGA  CGATCTGTCA  GAGTCTTAAG  AGTGATTTGG  TTCCCCATCC  CCCCTCCAAC    660
TGGAGTCTCC  TCCTCACTAT  TGATGTGTGC  ATCTGAGACC  CCCATCCCCG  CACCGAGTTT    720
CCCCATCTCT  GTCAGTAAAG  AGCAAGGCTT  CCAGAGACAA  CCCTCTAATA  GCGCGTCAGT    780
CCCGAATCTT  GAGTGGGATG  CGGGACTCCC  GTGCTATTTC  TTGGCGGAGG  TCTTTCCTGG    840
TCCTTATGGA  CACCCCTGGT  TTGGGATATG  GGGGCCGCTA  AGATTTCAGA  GATGGGGTCC    900
CTAGGCTGAG  NCCGCGTTTT  CCCGGGCAGC  GGTCGCGCTA  GAACCTTTCT  GGGCGGACCT    960
TCAGCCCCGC  GTGGCGCTCG  TGGAGCGCGG  GGGCTCGCTG  TGGCTCAACT  GCAGCACTAA    1020
CTGTCCGAGG  CCGGAGCGCG  GTGGCCTGGA  GACCTCGCTA  CGCCGAAACG  GGACCCAGAG    1080
GGGTCTGNAC  TGNCTGGCTC  GACAGCTGGT  GGACATCCGA  GANCCTGAAA  CCCAGCCGGT    1140
```

```
CTGCTTCTTC CNCTGCGCGC GCCGCACACT CCAAGCGCGT GGGCTCATCC GAACTTTCCG   1200
TGAGTTCAGG GTGGGCACNC CCCTTGGGTC TCTGGACCTC CCCCTCAAGC TCCTCCCACC   1260
CGCCCTCTGA TCCTCCTGCT TGTTCTGAAA GTACTACAGC TGGCTAGAGC GGAGTTTTTG   1320
GTCCCTTGCA GAGCGACCGG ATCGGGTAGA GCTAGTGCCT CTGCCTCCTT GGCAGCCTGT   1380
AGGTGAGAAC TTCACCTTGA GCTGCAGGGT CCCGGGGGCA GGACCCCGAG CGAGCCTCAC   1440
ATTGACCTTG CTGCGAGGCG GCCAGGAGCT GATTCGCCGA AGTTTCGTAG GCGAGCCACC   1500
CCGAGCTCGG GGTGCGATGC TCACCGCCAC GGTCCTGGCG CGCAGAGAGG ATCACAGGGC   1560
CAATTTCTCA TGCCTCGCGG AGCTTGACCT GCGNCCACAC GGCTTGGGAC TGTTTGCANA   1620
CAGCTCAGCC CCCAGACAGC TCCGCACGTT TGGTGAGTGT GGACCCTAAC TGACAGATTT   1680
TAAGAAGTTT AGGGCAGCCA GGCGTGGTGG CATGGTGTCG TAGGCCCTAA GTCCCAGCCC   1740
AAGCAGANCT AAGNCGGATC TCTTGTGAAT TAAAAGTCTA GCTCGTCTAC ATAACGAGGN   1800
CTGCATAGTT AAATCCCCCA AAAGTCTAAG CAGCTAGCCC TTACTTCCAA CACAAGTACT   1860
AGCTTAAGTA CTTTCTCCTG TGAGCTTTTT CCTTTATGTA TTTACTCGTT GAGAGAAAAA   1920
GAGAGTGTGT GTACGTGCCT TTATGCACAT GCCGCAGTGC TTGTATGGAA GTTAAAGAAT   1980
AAGGAGGCGT TCTGCCCTTC CATCCTGTGG GTCCTAGGGG TGGTATTAGC TCCTCAGGCT   2040
TTGTTAGTNA CAAGCGCCTA GGCTTGGGGA GCCATCTCGC CCGCTCCTCT GTATCTTTAG   2100
GGTGAAACCA GACAATGCAT GCAAATTGGT TGATCAACAC TGAATGTTTA GTTCGTAAAT   2160
TCAAGCTCTG TTCTTTGTCT TCCTCAGCCA TGCCTCCACT TTCCCCGAG CCTTATTGCC    2220
CCACGATTCT TAGAAGTGGG CTCAGAAAGG CCGGTGACKT GCACTTTGGA TGGACTGTTT   2280
CCTGCCCCAG AAGCCGGGGT TTACTTCTCT CTGGGAGATC AGAGGCTTCA TCCTAATGTG   2340
ACCCTCGACG GGGAGAGCCT TGTGGCCACT GCCACAGCTA CAGCAAGTGA AGAACAGGAA   2400
GGCACCAAAC AGCTGATGTG CATCGTGACC CTCGGGGGCG AAAGCAGGGA GACCCAGGAA   2460
AACCTGACTG TCTACAGTAA GGGGAATCCA ACAAGACCTT CAATAGCTCA GACTGGGGCT   2520
GGGGCTGGGT CTGGGTCTGG GGCCAGAGTC TCACAAAGGC GGAGCCTATA AAGTGGGCGG   2580
GACCTCCACA CCAGAACAAG CCGGGCGGGA GAGTTCCAGG GCAGGAGCAG ATAGAAGTTG   2640
GAAATTAATA GATTGGGTTG AGTTCCCTGA GTGGGGAGTG AACCCACCC AATTCTCTGT    2700
CCCCAGGCTT CCCGGCTCCT CTTCTGACTT TAAGTGAGCC AGAAGCCCCC GAGGGAAAGA   2760
TGGTGACCGT AAGCTGCTGG GCAGGGCCC GAGCCCTTGT CACCTTGGAG GGAATTCCAG    2820
CTGCGGTCCC TGGGCAGCCC GCTGAGCTCC AGTTAAATGT CACAAAGAAT GACGACAAGC   2880
GGGGCTTCTT CTGCGACGCT GCCCTCGATG TGGACGGGGA AACTCTGAGA AAGAACCAGA   2940
GCTCTGAGCT TCGTGTTCTG TGTGAGTGGA TGTTCACTTT ATCTCTGTGA ATTCCAAGGA   3000
CCCTCTTACC GGCCCCATCT TTAACCTTAT CGTATCCCCT CTGCCTCATG CCCGCAGACG   3060
CACCTCGGCT GGATGACTTG GACTGTCCCA GGAGCTGGAC GTGGCCAGAG GGTCCAGAGC   3120
AGACCCTCCA CTGCGAGGCC CGTGGAAACC CTGAGCCCTC CGTGCACTGT GCAAGGCCTG   3180
ACGGTGGGGC GGTGCTAGCG CTGGGCCTGT TGGGTCCAGT GACCCGTGCC CTCGCGGGCA   3240
CTTACCGATG TACAGCAATC AATGGGCAAG GCCAGGCGGT CAAGGATGTG ACCCTGACTG   3300
TGGAATGTGA GTAGGGGGAG GTGGGCATGC TTATCCCTTT AAGGTCACGG AGTGTACTGG   3360
GAGACTGGCT ATACGGAAAG GAAAGAAGCC TAGGTTCAGC AGGGATTGGG AAAACACTGA   3420
AGGAAAGTGG TGTGGTGTTT ACAAACTTAA CGGTGGTAAC TGGGCACGGT CTGGCAAAAA   3480
CAGACAGCCA AGAGAGTGTG CCTGGGAAGC TGCAATGGGG GCTTTGTGGG AATTGGTCAA   3540
```

```
CAGCACCCTG AGATCTCAGG AAAGGGGCCT GAAGTTATCT CCAGAACCCA TGTGAAGGCA    3600
GGAAGAGAGA ACGCCCACCT TTTCCTGCTC CCCCAACCC CCCCCACAT ATCACACGGA      3660
GTATATAAAT AAATAAAATG GCTCCTGCCG GAGGGAGTGA GAAGCTGTCT CCTGCAGGCT    3720
CAGAGCAGTG GTAGTGCATG CCTTTAATCC CAGCACTCGG TAGGCAAAGG CAGGCAGATC    3780
TCTGTGAATG TGGGGCCAGC CTGGTCTGTA CAGAGAAATC CTGTCTCAAA ACAAACCAGC    3840
AAAGAAACAA AACCAAAATC AATTCCAGAT GCCCAGCGC TGGACAGTGT AGGCTGCCCA     3900
NGACGTATTA CTTGNCTGGA GGGGACAGAG GCATCGCTTA GCTGTGTGGC ACACGGGTC     3960
CCACCACCTA GCGTGAGCTG TGTGCGCTCT GGAAAGGAGG AAGTCATGGA AGGGCCCTG     4020
CGTGTGGCCC GGGAGCACGC TGGCACTTAC CGATGCGAAG CCATCAACGC CAGGGATCA     4080
GCGGNCAAAA ATGTGGCTGT CACGGTGGAA TGTGAGTAGG GGTGGCTACG GAAATGTCCA    4140
CACCTGCGTC CTCTGTCCTC AGTGTGAACT CCTATTTCCC TGCTTCCTAG ATGGTCCCAG    4200
TTNTGAGGAG TTGGGCTGCC CCAGCAACTG GACTTGGGTA GAAGGATCTG GAAAACTGTT    4260
TTCCTGTGAA GTTGATGGGA AGCCGGAACC ACGCGTGGAG TGCGTGGGCT CGGAGGGTGC    4320
AAGCGAAGGG GTAGTGTTGC CCCTGGTGTC CTCGAACTCT GGTTCCAGAA ACTCTATGAC    4380
TCCTGGTAAC CTGTCACCGG GTATTTACCT CTGCAACGCC ACCAACCGGC ATGGCTCCAC    4440
AGTCAAAACA GTCGTCGTGA GCGCGGAATG TGAGCAGGGG CCCAGGTGGG CGGAGAGTAC    4500
CGGGTGTCCC AGGATCTTTT CTTTCCCTGA TGCCCCTCCT TATGGTGGCT GATCTGCAGC    4560
ACCGCCACAG ATGGATGAAT CCAGTTGCCC GAGTCACCAG ACATGGCTGG AAGGAGCCGA    4620
GGCTACTGCG CTGGCCTGCA GTGACAGGGG NCGCCCTCT CCACGCGTGC GCTGTTCCAG     4680
GGAAGGTGCA GCCAGGCTGG AGAGGCTACA GGTGTCCCGA GAGGATGCGG GGACCTACCT    4740
GTGTGTGGCT ACCAACGCGC ATGGCACGGA TTCACGGACC GTCACTGTGG GTGTGGAATG    4800
TGAGTGAGGA CAGCGCTGAA TGAAGACGAC TCAGACCGCC AGAAAAGTGC CTTGAGGCCT    4860
GGGATGTATG ATCCAGTGGG TAGAGTGCTC AATTAGCACT CACTAAAATG TATATTCTAT    4920
TCCTAATACT CTTTAATTTT ANCCTTTGGG AGGCAGAGAC AGGCAGATCT CTGTTCCGGG    4980
ATAACCTGCT CTCTGTCTAG GACAGCTTGG TCTACAGAGG GGNTACAGGC CCCCCCTCCC    5040
AAGATTGNAT AGCAACCCTC TGGCTCCCTG TCTCTCT                             5077
```

(2) INFORMATION FOR SEQ ID NO:9:

(i) SEQUENCE CHARACTERISTICS:
        (A) LENGTH: 1472 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
NGAATTCCGG CGGATCGGGT AGAGCTAGTG CCTCTGCCTC CTTGGCAGCC TGTAGGTGAG    60
AACTTCACCT TGAGCTGCAG GGTCCCGGGG GCAGGACCCC GAGCGAGCCT CACATTGACC    120
TTGCTGCGAG GCGGCCAGGA GCTGATTCGC CGAAGTTTCG TAGGCGAGCC ACCCCGAGCT    180
CGGGGTGCGA TGCTCACCGC CACGGTCCTG GCGCGCAGAG AGGATCACAG GGCCAATTTC    240
TCATGCCTCG CGGAGCTTGA CCTGCGGCCA CACGGCTTGG GACTGTTTGC AAACAGCTCA    300
GCCCCCAGAC AGCTCCGCAC GTTTGCCATG CCTCCACTTT CCCCGAGCCT TATTGCCCCA    360
CGATTCTTAG AAGTGGGCTC AGAAAGGCCG GTGACTTGCA CTTTGGATGG ACTGTTTCCT    420
```

| | | | | | |
|---|---|---|---|---|---|
| GCCCCAGAAG | CCGGGGTTTA | CCTCTCTCTG | GGAGATCAGA | GGCTTCATCC | TAATGTGACC | 480
| CTCGACGGGG | AGAGCCTTGT | GGCCACTGCC | ACAGCTACAG | CAAGTGAAGA | ACAGGAAGGC | 540
| ACCAAACAGC | TGATGTGCAT | CGTGACCCTC | GGGGGCGAAA | GCAGGGAGAC | CCAGGAAAAC | 600
| CTGACTGTCT | ACAGCTTCCC | GGCTCCTCTT | CTGACTTTAA | GTGAGCCAGA | AGCCCCGAG | 660
| GGAAAGATGG | TGACCGTAAG | CTGCTGGGCA | GGGGCCCGAG | CCCTTGTCAC | CTTGGAGGGA | 720
| ATTCCAGCTG | CGGTCCCTGG | GCAGCCCGCT | GAGCTCCAGT | TAAATGTCAC | AAAGAATGAC | 780
| GACAAGCGGG | GCTTCTTCTG | CGACGCTGCC | CTCGATGTGG | ACGGGAAAC | TCTGAGAAAG | 840
| AACCAGAGCT | CTGAGCTTCG | TGTTCTGTGT | GAGTGGATGT | TCACTTTATC | TCTGTGAATT | 900
| CCAAGGACCC | TCTTACCGGC | CCCATCTTTA | ACCTTATCGT | ATCCCTCTG | CCTCATGCCC | 960
| GCAGACGCAC | CTCGGCTGGA | TGACTTGGAC | TGTCCCAGGA | GCTGGACGTG | GCCAGAGGGT | 1020
| CCAGAGCAGA | CCCTCCACTG | CGAGGCCCGT | GGAAACCCTG | AGCCCTCCGT | GCACTGTGCA | 1080
| AGGCCTGACG | GTGGGGCGGT | GCTAGCGCTG | GGCCTGTTGG | GTCCAGTGAC | CCGTGCCCTC | 1140
| GCGGGCACTT | ACCGATGTAC | AGCAATCAAT | GGGCAAGGCC | AGGCGGTCAA | GGATGTGACC | 1200
| CTGACTGTGG | AATATGCCCC | AGCGCTGGAC | AGTGTAGGCT | GCCAGAACG | TATTACTTGG | 1260
| CTGGAGGGGA | CAGAGGCATC | GCTTAGCTGT | GTGGCACACG | GGTCCCACC | ACCTAGCGTG | 1320
| AGCTGTGTGC | GCTCTGGAAA | GGAGGAAGTC | ATGGAAGGGC | CCCTGCGTTT | TGGCCGGGAG | 1380
| CACGCTGGCA | CTTACCGATG | CGAAGCCATC | AACGCCAGGG | GATCAGCGGC | CAAAAATGTG | 1440
| GCTGTCACGG | TGGAATATGG | TCCCCGGAAT | TC | | | 1472 |

( 2 ) INFORMATION FOR SEQ ID NO:10:

( i ) SEQUENCE CHARACTERISTICS:
        ( A ) LENGTH: 2550 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

| | | | | | |
|---|---|---|---|---|---|
| CCTCTGCCTC | CTTGGCAGCC | TGTAGGTGAG | AACTTCACCT | TGAGCTGCAG | GGTCCCGGGG | 60
| GCAGGACCCC | GAGCGAGCCT | CACATTGACC | TTGCTGCGAG | GCGGCCAGGA | GCTGATTCGC | 120
| CGAAGTTTCG | TAGGCGAGCC | ACCCCGAGCT | CGGGGTGCGA | TGCTCACCGC | CACGGTCCTG | 180
| GCGCGCAGAG | AGGATCACAG | GGCCAATTTC | TCATGCCTCG | CGGAGCTTGA | CCTGCGGCCA | 240
| CACGGCTTGG | GACTGTTTGC | AAACAGCTCA | GCCCCAGAC | AGCTCCGCAC | GTTTGCCATG | 300
| CCTCCACTTT | CCCCGAGCCT | TATTGCCCCA | CGATTCTTAG | AAGTGGGCTC | AGAAAGGCCG | 360
| GTGACTTGCA | CTTTGGATGG | ACTGTTTCCT | GCCCCAGAAG | CCGGGGTTTA | CCTCTCTCTG | 420
| GGAGATCAGA | GGCTTCATCC | TAATGTGACC | CTCGACGGGG | AGAGCCTTGT | GGCCACTGCC | 480
| ACAGCTACAG | CAAGTGAAGA | ACAGGAAGGC | ACCAAACAGC | TGATGTGCAT | CGTGACCCTC | 540
| GGGGGCGAAA | GCAGGGAGAC | CCAGGAAAAC | CTGACTGTCT | ACAGCTTCCC | GGCTCCTCTT | 600
| CTGACTTTAA | GTGAGCCAGA | AGCCCCGAG | GGAAAGATGG | TGACCGTAAG | CTGCTGGGCA | 660
| GGGGCCCGAG | CCCTTGTCAC | CTTGGAGGGA | ATTCCAGCTG | CGGTCCCTGG | GCAGCCCGCT | 720
| GAGCTCCAGT | TAAATGTCAC | AAAGAATGAC | GACAAGCGGG | GCTTCTTCTG | CGACGCTGCC | 780
| CTCGATGTGG | ACGGGAAAC | TCTGAGAAAG | AACCAGAGCT | CTGAGCTTCG | TGTTCTGTAC | 840
| GCACCTCGGC | TGGATGACTT | GGACTGTCCC | AGGAGCTGGA | CGTGGCCAGA | GGGTCCAGAG | 900
| CAGACCCTCC | ACTGCGAGGC | CCGTGGAAAC | CCTGAGCCCT | CCGTGCACTG | TGCAAGGCCT | 960

```
GACGGTGGGG CGGTGCTAGC GCTGGGCCTG TTGGGTCCAG TGACCCGTGC CCTCGCGGGC    1020

ACTTACCGAT GTACAGCAAT CAATGGGCAA GGCCAGGCGG TCAAGGATGT GACCCTGACT    1080

GTGGAATATG CCCCAGCGCT GGACAGTGTA GGCTGCCCAG AACGTATTAC TTGGCTGGAG    1140

GGGACAGAGG CATCGCTTAG CTGTGTGGCA CACGGGGTCC CACCACCTAG CGTGAGCTGT    1200

GTGCGCTCTG GAAAGGAGGA AGTCATGGAA GGGCCCCTGC GTGTGGCCCG GAGCACGCT     1260

GGCACTTACC GATGCGAAGC CATCAACGCC AGGGGATCAG CGGCCAAAAA TGTGGCTGTC    1320

ACGGTGGAAT ATGGTCCCAG TTTTGAGGAG TTGGGCTGCC CCAGCAACTG GACTTGGGTA    1380

GAAGGATCTG GAAAACTGTT TTCCTGTGAA GTTGATGGGA AGCCGGAACC ACGCGTGGAG    1440

TGCGTGGGCT CGGAGGGTGC AAGCGAAGGG GTAGTGTTGC CCCTGGTGTC CTCGAACTCT    1500

GGTTCCAGAA ACTCTATGAC TCCTGGTAAC CTGTCACCGG GTATTTACCT CTGCAACGCC    1560

ACCAACCGGC ATGGCTCCAC AGTCAAAACA GTCGTCGTGA GCGCGGAATC ACCGCCACAG    1620

ATGGATGAAT CCAGTTGCCC GAGTCACCAG ACATGGCTGG AAGGAGCCGA GGCTACTGCG    1680

CTGGCCTGCA GTGCCAGAGG CCGCCCCTCT CCACGCGTGC GCTGTTCCAG GGAAGGTGCA    1740

GCCAGGCTGG AGAGGCTACA GGTGTCCCGA GAGGATGCGG GGACCTACCT GTGTGTGGCT    1800

ACCAACGCGC ATGGCACGGA TTCACGGACC GTCACTGTGG GTGTGGAATA CCGGCCTGTG    1860

GTGGCTGAGC TGGCAGCCTC GCCCCCAAGC GTGCGGCCTG GCGGAAACTT CACTCTGACC    1920

TGCCGTGCAG AGGCCTGGCC TCCAGCCCAG ATCAGCTGGC GCGCGCCCCC GGGAGCTCTC    1980

AACCTCGGTC TCTCCAGCAA CAACAGCACG CTGAGCGTGG CGGGTGCCAT GGGCAGCCAT    2040

GGTGGCGAGT ATGAGTGCGC AGCCACCAAT GCGCATGGGC GCCACGCACG GCGCATCACG    2100

GTGCGCGTGG CCGGTCCATG GCTGTGGGTC GCTGTGGGCG GTGCGGCAGG GGGCGCGGCG    2160

CTGCTGGCCG CAGGGGCCGG CCTGGCCTTC TACGTGCAGT CCACCGCTTG CAAGAAGGGA    2220

GAGTACAACG TCCAGGAGGC TGAGAGCTCA GGCGAGGCGG TGTGTCTCAA TGGCGCGGGC    2280

GGGACACCGG GTGCAGAAGG CGGAGCAGAG ACCCCCGGCA CTGCCGAGTC ACCTGCAGAT    2340

GGCGAGGTTT TCGCCATCCA GCTGACATCT TCCTGAGCCT GTATCCAGCT CCCCCAGGGG    2400

CCTCGAAAGC ACAGGGGTGG ACGTATGTAT TGTTCACTCT CTATTTATTC AACTCCAGGG    2460

GCGTCGTCCC CGTTTCTAC CCATTCCCTT AATAAAGTTT TTATAGGAGA AAAAAAAAA     2520

AAAAAAAAA AAAAAAAAA AAAAAAAAA                                        2550
```

( 2 ) INFORMATION FOR SEQ ID NO:11:

( i ) SEQUENCE CHARACTERISTICS:
        ( A ) LENGTH: 222 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
AATTCGATCA CTCGCGCTCC CCTCGCCTTC TGCGCTCTCC CCTCCCTGGC AGCGGCGGCA     60

ATGCCGGGGC CTTCACCAGG GCTGCGCCGA CGCTCCTCG GCCTCTGGGC TGCCCTGGGC     120

CTGGGGATCC TAGGCATCTC AGCGGTCGCG CTAGAACCTT TCTGGGCGGA CCTTCAGCCC    180

CGCGTGGCGC TCGTGGAGCG CGGGGCTCG CTGTGGCTCA AC                        222
```

( 2 ) INFORMATION FOR SEQ ID NO:12:

( i ) SEQUENCE CHARACTERISTICS:

( A ) LENGTH: 292 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:12:

| | | | | | | |
|---|---|---|---|---|---|---|
| TGTGGAGCTG | GCACCCCTGC | CTCCTTGGCA | GCCGGTGGGC | CAGAACTTCA | CCCTGCGCTG | 60 |
| CCAAGTGGAG | GGTGGGTCGC | CCCGGACCAG | CCTCACGGTG | GTGCTGCTTC | GCTGGGAGGA | 120 |
| GGAGCTGAGC | CGGCAGCCCG | CAGTGGAGGA | GCCAGCGGAG | GTCACTGCCA | CTGTGCTGGC | 180 |
| CAGCAGAGAC | GACCACGGAG | CCCCTTTCTC | ATGCCGCACA | GAACTGGACA | TGCAGCCCCA | 240 |
| GGGGCTGGGA | CTGTTCGTGA | ACACCTCAGC | CCCCCGCCAG | CTCCGAACCT | TT | 292 |

( 2 ) INFORMATION FOR SEQ ID NO:13:

( i ) SEQUENCE CHARACTERISTICS:
( A ) LENGTH: 105 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:13:

| Pro | Asp | Arg | Val | Glu | Leu | Val | Pro | Leu | Pro | Pro | Trp | Gln | Pro | Val | Gly |
|---|---|---|---|---|---|---|---|---|---|---|---|---|---|---|---|
| 1 | | | | 5 | | | | | 10 | | | | | 15 | |

| Glu | Asn | Phe | Thr | Leu | Ser | Cys | Arg | Val | Pro | Gly | Ala | Gly | Pro | Arg | Ala |
|---|---|---|---|---|---|---|---|---|---|---|---|---|---|---|---|
| | | | 20 | | | | | 25 | | | | 30 | | | |

| Ser | Leu | Thr | Leu | Thr | Leu | Leu | Arg | Gly | Gly | Gln | Glu | Leu | Ile | Arg | Arg |
|---|---|---|---|---|---|---|---|---|---|---|---|---|---|---|---|
| | | 35 | | | | | 40 | | | | | 45 | | | |

| Ser | Phe | Val | Gly | Glu | Pro | Pro | Arg | Ala | Arg | Cys | Ala | Met | Leu | Thr | Ala |
|---|---|---|---|---|---|---|---|---|---|---|---|---|---|---|---|
| | 50 | | | | | 55 | | | | | 60 | | | | |

| Thr | Val | Leu | Ala | Arg | Arg | Glu | Asp | His | Arg | Asp | Asn | Phe | Ser | Cys | Leu |
|---|---|---|---|---|---|---|---|---|---|---|---|---|---|---|---|
| 65 | | | | | 70 | | | | | 75 | | | | | 80 |

| Ala | Glu | Leu | Asp | Leu | Arg | Thr | His | Gly | Leu | Gly | Leu | Phe | Ala | Asn | Ser |
|---|---|---|---|---|---|---|---|---|---|---|---|---|---|---|---|
| | | | | 85 | | | | | 90 | | | | | 95 | |

| Ser | Ala | Pro | Arg | Gln | Leu | Arg | Thr | Phe |
|---|---|---|---|---|---|---|---|---|
| | | | 100 | | | | | 105 |

( 2 ) INFORMATION FOR SEQ ID NO:14:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:14:

GAACTCGAGG CCATGCCTCC ACTTTCC   27

( 2 ) INFORMATION FOR SEQ ID NO:15:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:15:

CCATAAGCTT TATTCCACCG TGACAGCCAC                                              30

( 2 ) INFORMATION FOR SEQ ID NO:16:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

AACGTGCGGA GCTGTCTG                                                           18

( 2 ) INFORMATION FOR SEQ ID NO:17:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:17:

ACGGAATTCG AAGCCATCAA CGCCAGG                                                 27

( 2 ) INFORMATION FOR SEQ ID NO:18:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:18:

CATGAATTCC GAATCTTGAG TGGGATG                                                 27

( 2 ) INFORMATION FOR SEQ ID NO:19:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:19:

ATAGAATTCC TCGGGACACC TGTAGCC                                                 27

( 2 ) INFORMATION FOR SEQ ID NO:20:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:20:

CARGGTGACA AGGGCTCG                                                           18

( 2 ) INFORMATION FOR SEQ ID NO:21:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:21:

TATGAATTCA GTTGAGCCAC AGCGAGC    27

( 2 ) INFORMATION FOR SEQ ID NO:22:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:22:

CCGGGTCCTA GAGGTGGACA CGCA    24

( 2 ) INFORMATION FOR SEQ ID NO:23:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:23:

TGCAGTGTCT CCTGGCTCTG GTTC    24

ICAM-4 MATERIALS AND METHODS

This application is a continuation-in-part of U.S. patent application Ser. No. 08/102,852, now abandoned, filed Aug. 5, 1993 as a continuation-in-part of U.S. patent application Ser. No. 08/009,266, now abandoned, filed Jan. 22, 1993 as a continuation-in-part of U.S. patent application Ser. No. 07/894,061, now abandoned, filed Jun. 5, 1992 as a continuation-in-part of U.S. patent application Ser. No. 7/889,724, now abandoned, filed May 26, 1992 as a continuation-in-part of U.S. patent application Ser. No. 07/827,689, now abandoned, filed Jan. 27, 1992.

FIELD OF THE INVENTION

The present invention relates generally to cellular adhesion molecules and more particularly to the cloning and expression of DNA encoding a heretofore unknown polypeptide designated "ICAM-4" which possesses structural relatedness to the intercellular adhesion molecules ICAM-1, ICAM-2, and ICAM-3.

BACKGROUND OF THE INVENTION

Research spanning the last decade has significantly elucidated the molecular events attending cell-cell interactions in the body, especially those events involved in the movement and activation of cells in the immune system, and more recently, those involved in development and normal physiological function of cells in the nervous system. See generally, Springer, *Nature*, 346: 425–434 (1990) regarding cells of the immune system, and Yoshihara, et al. *Neurosci. Res.* 10:83–105 (1991) and Sonderegger and Rathjen, *J. Cell Biol.* 119:1387–1394 (1992) regarding cells of the nervous system. Cell surface proteins, and especially the so-called Cellular Adhesion Molecules ("CAMs") have correspondingly been the subject of pharmaceutical research and development having as its goal intervention in the processes of leukocyte extravasation to sites of inflammation and leukocyte movement to distinct target tissues, as well as neuronal differentiation and formation of complex neuronal circuitry. The isolation and characterization of cellular adhesion molecules, the cloning and expression of DNA sequences encoding such molecules, and the development of therapeutic and diagnostic agents relevant to inflammatory processes and development and function of the nervous system have also been the subject of numerous U.S. and foreign applications for Letters Patent. See Edwards, *Current Opinion in Therapeutic Patents*, 1(11): 1617–1630 (1991) and particularly the published "patent literature references" cited therein.

Of fundamental interest to the background of the present invention are the prior identification and characterization of certain mediators of cell adhesion events, the "leukointegrins," LFA-1, MAC-1 and gp 150.95 (referred to in WHO nomenclature as CD18/CD11a, CD18/CD11b, and CD18/CD11c, respectively) which form a subfamily of heterodimeric "integrin" cell surface proteins present on B lymphocytes, T lymphocytes, monocytes and granulocytes. See, e.g., Table 1 of Springer, supra, at page 429. Also of interest are other single chain adhesion molecules (CAMs) that have been implicated in leukocyte activation, adhesion, motility and the like, which are events attendant to the inflammatory process. For example, it is presently believed that prior to the leukocyte extravasation which characterizes inflammatory processes, activation of integrins constitutively expressed on leukocytes occurs and is followed by a tight ligand/receptor interaction between the integrins (e.g., LFA-1) and one or both of two distinct intercellular adhesion molecules (ICAMs) designated ICAM-1 and ICAM-2 which are expressed on blood vessel endothelial cell surfaces and on other leukocytes.

Like the other CAMs characterized to date, [e.g., vascular adhesion molecule (VCAM-1) as described in PCT WO 90/13300 published Nov. 15, 1990; and platelet endothelial cell adhesion molecule (PECAM-1) as described in Newman et al., *Science*, 247:1219–1222 (1990) and PCT WO 91/10683 published Jul. 25, 1991], ICAM-1 and ICAM-2 are structurally homologous to other members of the immunoglobulin gene superfamily in that the extracellular portion of each is comprised of a series of domains sharing a similar carboxy terminal motif. A "typical" immunoglobulin-like domain contains a loop structure usually anchored by a disulfide bond between two cysteines at the extremity of each loop. ICAM-1 includes five immunoglobulin-like domains; ICAM-2, which differs from ICAM-1 in terms of cell distribution, includes two such domains; PECAM-1 includes six; VCAM includes six or seven, depending on splice variations, and so on. Moreover, CAMs typically include a hydrophobic "transmembrane" region believed to participate in orientation of the molecule at the cell surface and a carboxy terminal "cytoplasmic" region. Graphic models of the operative disposition of CAMs generally show the molecule anchored in the cell membrane at the transmembrane region with the cytoplasmic "tail" extending into the cell cytoplasm and one or more immunoglobulin-like loops extending outward from the cell surface.

A number of neuronal cells express surface receptors with extracellular Ig-like domains, structurally similarity to the ICAMs. See for example, Yoshihara, et al., supra. In addition to Ig-like domains, many adhesion molecules of the nervous system also contain tandemly repeated fibronectin-like sequences in the extracellular domain.

A variety of therapeutic uses has been projected for intercellular adhesion molecules, including uses premised on the ability of ICAM-1 to bind human rhinovirus. European Patent Application 468 257 A published Jan. 29, 1992, for example, addresses the development of multimeric configurations and forms of ICAM-1 (including full length and truncated molecular forms) proposed to have enhanced ligand/receptor binding activity, especially in binding to viruses, lymphocyte associated antigens and pathogens such as *Plasmodium falciparum*.

In a like manner, a variety of uses has been projected for proteins immunologically related to intercellular adhesion molecules. WO91/16928, published Nov. 14, 1991, for example, addresses humanized chimeric anti-ICAM-1 antibodies and their use in treatment of specific and non-specific inflammation, viral infection and asthma. Anti-ICAM-1 antibodies and fragments thereof are described as useful in treatment of endotoxic shock in WO92/04034, published Mar. 19, 1992. Inhibition of ICAM-1 dependent inflammatory responses with anti-ICAM-1 anti-idiotypic antibodies and antibody fragments is addressed in WO92/06119, published Apr. 16, 1992.

Despite the fundamental insights into cell adhesion phenomena which have been gained by the identification and characterization of intercellular adhesion proteins such as ICAM-1 and lymphocyte interactive integrins such as LFA-1, the picture is far from complete. It is generally believed that numerous other proteins are involved in inflammatory processes and in targeted lymphocyte movement throughout the body. For example, U.S. patent application Ser. Nos. 07/827,689, 07/889,724, 07/894,061 and 08/009,266 all now abandoned, and corresponding published PCT Application WO 93/14776 (published Aug. 5, 1993) disclose the cloning and expression of an ICAM-Related protein, ICAM-R, now commonly referred to as ICAM-3. The disclosures of these applications are specifically incorporated by reference herein and the DNA and amino acid sequences of ICAM-R (ICAM-3) are set out in SEQ ID NO: 4 herein. This new ligand has been found to be expressed on human lymphocytes, monocytes and granulocytes.

Of particular interest to the present application, still another ICAM-like surface molecule was identified which has a tissue specific expression unlike that of any known ICAM molecule. Mori, et al., [*Proc. Natl. Acad. Sci. (USA)* 84:3921–3925 (1987)] reported identification of a telencephalon-specific antigen in rabbit brain, specifically immunoreactive with monoclonal antibody 271A6. This surface antigen was named telencephalin. Imamura, et al., [Neurosci. Letts. 119:118–121 (1990)], using a polyclonal antibody to assess localized expression, asserted that expression of telencephalin in visual cortex of cats showed variation in layers of the tissue, and also reported telencephalin expression was variable as a function of development. Oka, et al., [Neuroscience 35:93–103 (1990)] subsequently reported isolation of telencephalin using monoclonal antibody 271A6. The publication reports a molecular weight for the surface molecule of about 500 kD and that the molecule was composed of four subunits, each with a native molecular weight of 130 kD and approximately 100 kD following N-glycanase treatment. Yoshihiro, et al., [*Neuroscience, Research Supplement* 18, p. S83 (1994)], reported the cDNA and amino acid sequences for rabbit telencephalin at the 17th Annual Meeting of the Japan Neuroscience Society in Nagoya, Japan, Dec. 7–9, 1993, and the 23rd Annual Meeting of the Society for Neuroscience in Washington, D.C., Nov. 9, 1993 [Society for Neuroscience Abstracts 19 (1–3) p. 646 (1993)]. The deduced amino acid sequence reported suggested that the 130 kD telencephalon is an integral membrane protein with nine extracellular immunoglobulin (Ig)-like domains. The distal eight of these domains showed homology to other ICAM Ig-like domains. This same information was reported by Yoshihara, et al., in *Neuron* 12:543–553 (1994).

There thus continues to be a need in the art for the discovery of additional proteins participating in human cell-cell interactions and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. Such seminal information would inter alia, provide for the large scale production of the proteins, allow for the identification of cells naturally producing them, and permit the preparation of antibody substances or other novel binding proteins specifically reactive therewith and/or inhibitory of ligand/receptor binding reactions in which they are involved.

BRIEF SUMMARY OF THE INVENTION

In one of its aspects, the present invention provides purified and isolated polynucleotides (e.g., DNA sequences and RNA transcripts thereof) encoding a novel polypeptide, "ICAM-4," as well as polypeptide variants (including fragments and deletion, substitution, and addition analogs) thereof which display one or more ligand/receptor binding biological activities and/or immunological properties specific to ICAM-4. ICAM-4-specific ligand/receptor binding biological activities encompass interactions of both the ICAM-4 extracellular and cytoplasmic domains with other molecules (e.g., in processes of cell-cell adhesion and/or signal transduction). Preferred DNA sequences of the invention include genomic and cDNA sequences as well as wholly or partially chemically synthesized DNA sequences. A presently preferred polynucleotide is set out in SEQ ID NO: 1 and encodes rat species ICAM-4. Biological replicas (i.e., copies of isolated DNA sequences made in vivo or in vitro) of DNA sequences of the invention are contemplated. Also provided are autonomously replicating recombinant constructions such as plasmid and viral DNA vectors incorporating ICAM-4 sequences and especially vectors wherein DNA encoding ICAM-4 or an ICAM-4 variant is operatively linked to an endogenous or exogenous expression control DNA sequence.

According to another aspect of the invention, host cells, especially unicellular host cells such as procaryotic and eucaryotic cells, are stably transformed with DNA sequences of the invention in a manner allowing the desired polypeptides to be expressed therein. Host cells expressing such ICAM-4 and ICAM-4 variant products can serve a variety of useful purposes. To the extent that the expressed products are "displayed" on host cell surfaces, the cells may constitute a valuable immunogen for the development of antibody substances specifically immunoreactive with ICAM-4 and ICAM-4 variants. Host cells of the invention are conspicuously useful in methods for the large scale production of ICAM-4 and ICAM-4 variants wherein the cells are grown in a suitable culture medium and the desired polypeptide products are isolated from the cells or from the medium in which the cells are grown.

Novel ICAM-4 of the invention may be obtained as isolates from natural cell sources, but, along with ICAM-4 variant products, are preferably produced by recombinant procedures involving host cells of the invention. A presently preferred amino acid sequence for an ICAM-4 polypeptide is set out in SEQ ID NO: 2. The products may be obtained in fully or partially glycosylated, partially or wholly de-glycosylated, or non-glycosylated forms, depending on the host cell selected for recombinant production and/or post-isolation processing. ICAM-4 variants of the invention may comprise water soluble or insoluble monomeric, multimeric or cyclic ICAM-4 fragments which include all or part of one or more of the domain regions specified above and having a biological or immunological property of ICAM-4 including, e.g., the ability to bind to a binding partner of ICAM-4 and/or inhibit binding of ICAM-4 to a natural binding partner. ICAM-4 variants of the invention may also comprise polypeptide analogs wherein one or more of the specified amino acids is deleted or replaced: (1) without loss, and preferably with enhancement, of one or more biological activities or immunological characteristics specific for ICAM-4; or (2) with specific disablement of a particular ligand/receptor binding function. Analog polypeptides including additional amino acid (e.g., lysine or cysteine) residues that facilitate multimer formation are contemplated.

Also comprehended by the present invention are antibody substances (e.g., monoclonal and polyclonal antibodies, antibody fragments, single chain antibodies, chimeric antibodies, CDR-grafted antibodies and the like) and other binding proteins (e.g., polypeptides and peptides) which are specific (i.e., non-reactive with the ICAM-1, ICAM-2, and ICAM-3 intercellular adhesion molecules to which ICAM-4 is structurally related) for ICAM-4 or ICAM-4 variants. Antibody substances can be developed using isolated natural or recombinant ICAM-4 or ICAM-4 variants or cells expressing such products on their surfaces. Binding proteins of the invention are additionally useful for characterization of binding site structure(s) (e.g., epitopes and/or sensitivity of binding properties to modifications in ICAM-4 amino acid sequence).

Binding proteins are useful, in turn, in compositions for immunization as well as for purifying polypeptides of the invention and identifying cells displaying the polypeptides on their surfaces. They are also manifestly useful in modulating (i.e., blocking, inhibiting or stimulating) ligand/receptor binding biological activities involving ICAM-4, especially those ICAM-4 effector functions involved in specific and non-specific immune system responses. Anti-idiotypic antibodies specific for anti-ICAM-4 antibody substances and uses of such anti-idiotypic antibody substances in modulating immune responses are also contemplated. Assays for the detection and quantification of ICAM-4 on cell surfaces and in fluids such as serum may involve, for example, a single antibody substance or multiple antibody substances in a "sandwich" assay format.

The scientific value of the information contributed through the disclosures of DNA and amino acid sequences of the present invention is manifest. As one series of examples, knowledge of the sequence of a cDNA for ICAM-4 makes possible the isolation by DNA/DNA hybridization of genomic DNA sequences encoding ICAM-4 and specifying ICAM-4 expression control regulatory sequences such as promoters, operators and the like. DNA/DNA hybridization procedures carried out with DNA sequences of the invention and under stringent conditions are likewise expected to allow the isolation of DNAs encoding allelic variants of ICAM-4, other structurally related proteins sharing one or more of the biological and/or immunological properties specific to ICAM-4, and proteins homologous to ICAM-4 from other species. DNAs of the invention are useful in DNA/RNA hybridization assays to detect the capacity of cells to synthesize ICAM-4. Also made available by the invention are anti-sense polynucleotides relevant to regulating expression of ICAM-4 by those cells which ordinarily express the same. As another series of examples, knowledge of the DNA and amino acid sequences of ICAM-4 makes possible the generation by recombinant means of ICAM-4 variants such as hybrid fusion proteins (sometimes referred to as "immunoadhesions") characterized by the presence of ICAM-4 protein sequences and immunoglobulin heavy chain constant regions and/or hinge regions. See, Capon et al., Nature, 337: 525–531 (1989); Ashkenazi et al., P.N.A.S. (USA), 88: 10535–10539 (1991); and PCT WO 89/02922, published Apr. 6, 1989. ICAM-4 variant fusion proteins may also include, for example, selected extracellular domains of ICAM-4 and portions of other cell adhesion molecules.

The DNA and amino acid sequence information provided by the present invention also makes possible the systematic analysis of the structure and function of ICAM-4 and definition of those molecules with which it will interact on extracellular and intracellular levels. The idiotypes of anti-ICAM-4 monoclonal antibodies of the invention are representative of such molecules and may mimic natural binding proteins (peptides and polypeptides) through which ICAM-4 intercellular and intracellular activities are modulated or by which ICAM-4 modulates intercellular and intracellular events. Alternately, they may represent new classes of modulators of ICAM-4 activities. Anti-idiotypic antibodies, in turn, may represent new classes of biologically active ICAM-4 equivalents. In vitro assays for identifying antibodies or other compounds that modulate the activity of ICAM-4 may involve, for example, immobilizing ICAM-4 or a natural ligand to which ICAM-4 binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of ICAM-4 binding. The DNA sequence information provided by the present invention also makes possible the development, by homologous recombination or "knockout" strategies [see, e.g., Capecchi, Science, 244: 1288–1292 (1989)], of rodents that fail to express a functional ICAM-4 protein or that express a variant ICAM-4 protein. Such rodents are useful as models for studying the activities of ICAM-4 and ICAM-4 modulators in vivo.

DETAILED DESCRIPTION OF THE INVENTION

The disclosures of parent U.S. patent application Ser. No. 08/102,852, filed Aug. 5, 1993, now abandoned, are specifically incorporated by reference. The examples of that application address, inter alia: design and construction of oligonucleotide probes for PCR amplification of ICAM related DNAs; use of the probes to amplify a human genomic fragment homologous to, but distinct from DNAs encoding ICAM-1 and ICAM-2; screening of cDNA libraries with the genomic fragment to isolate additional ICAM-R (ICAM-3) coding sequences; screening of cDNA libraries to isolate a full length human cDNA sequence encoding ICAM-3; characterization of DNA and amino acid sequence information for ICAM-3, especially as related to ICAM-1 and ICAM-2; development of mammalian host cells expressing ICAM-3; assessment of indications of ICAM-3 participation in adhesion events involving CD18-dependent and CD18-independent pathways; inhibition of cell adhesion to ICAM-3 by ICAM-3-derived peptides; expression of variants of ICAM-3; preparation and characterization of anti-ICAM-3 antibodies and fragments thereof; mapping of ICAM-3 epitopes recognized by anti-ICAM-3 monoclonal antibodies; assessment of the distribution and biochemical characterization of ICAM-3 and RNA encoding the same; assessment of ICAM-3 in homotypic cell-cell adhesion and immune cell activation/proliferation; characterization of ICAM-3 monoclonal antibodies; and assessment of differential phosphorylation and cytoskeletal associations of the cytoplasmic domain of ICAM-3. Also disclosed was the identification of a rodent ICAM-encoding DNA that, at the time, appeared to be the rat homolog of human ICAM-3, and the use of this DNA to construct and express DNAs encoding glutathione-S-transferase fusion proteins. The detailed description of how this rodent DNA was identified can be found in the parent application (U.S. Ser. No. 08/102,852 now abandoned) in Example 6, and is reproduced herein as Example 1. As more of the rodent ICAM-coding sequence was identified, it became apparent that the rodent ICAM DNA did not encode a rat species homolog of human ICAM-3, but, in fact, encoded a novel ICAM polypeptide, herein named ICAM-4. In order to appreciate the events which led to the identification of ICAM-4, a chronology is provided which is followed by a detailed description of the invention.

A first rodent genomic ICAM-4 sequence was identified which encoded a region homologous to domain 2 (herein SEQ ID NO: 3, and SEQ ID NO: 23 of U.S. Ser. No. 08/102,852) of human ICAM-3 (herein as SEQ ID NO: 4). A second, overlapping genomic DNA (herein SEQ ID NO:

5, and SEQ ID NO: 26 of U.S. Ser. No. 08/102,852 now abandoned) was also identified which encoded both the domain 2 region of SEQ ID NO: 3, and sequences for ICAM-1. Using SEQ ID NO: 3 as a probe, a rodent spleen cDNA (herein SEQ ID NO: 6, and SEQ ID NO: 25 in U.S. Ser. No. 08/102,852 now abandoned) was identified which encoded domains 2 through 5 as well as a fifth domain not previously observed as an ICAM domain. At this time, these newly identified rodent DNAs appeared to encode a rodent homolog of human ICAM-3, however alignment of 3' regions of these DNAs with other ICAMs proved difficult.

The subsequent isolation of a 1 kb cDNA clone from a rat spleen library, and amplification of an RT-PCR fragment indicated that a portion of both the cDNA and genomic clones had not been sequenced. Another RT-PCR amplification product (SEQ ID NO: 7) confirmed this omission. It was determined that a fragment of 177 bp was excised from the genomic and cDNA clones by EcoRI digestion of the clones to isolate these sequences from λ phage for DNA sequencing studies. Reanalysis of SEQ ID NOs: 5 and 6 in light of these other sequences permitted identification of more accurate and complete sequences for the originally isolated genomic and cDNA clones, presented in corrected form herein as SEQ ID NOs: 8 and 9.

In order to identify a complete coding sequence for ICAM-4, a rat brain cDNA (SEQ ID NO: 10) was isolated, and 5' end sequence determined by 5' rapid amplification of cDNA ends (5' RACE), the amplification product set forth in SEQ ID NO: 11. Combining information from the RT-PCR clone (SEQ ID NO: 7), the brain cDNA (SEQ ID NO: 10) and the RACE amplification product (SEQ ID NO: 1 1) permitted identification of the complete coding sequence for ICAM-4 (SEQ ID NO: 1).

The present invention is thus illustrated by the following examples. More particularly, Example 1 addresses cloning of a partial rodent ICAM-4 DNA. Example 2 describes Northern blot analysis of rodent ICAM-4 transcription. Example 3 describes isolation of a full length rodent ICAM-4 cDNA. Example 4 relates the in situ hybridization of rodent ICAM-4 in brain tissue. Example 5 addresses generation of ICAM-4 fusion proteins in prokaryotes. Example 6 describes production of monoclonal antibodies specific for ICAM-4. Example 7 describes expression of soluble ICAM-4 proteins in a baculovirus expression system. Example 8 relates to immunocytochemical analysis with ICAM-4-specific monoclonal antibodies. Example 9 addresses cloning of a human ICAM-4 DNA.

EXAMPLE 1

Cloning of Rat ICAM-Related DNA

A. Isolation of a Rat Genomic ICAM-Related Domain 2 DNA

A rat genomic library constructed in λ EMBL3 was screened with [$^{32}$P]-labeled probes generated by PCR from human ICAM-3 domain 2, the sequence of the probe as set forth in SEQ ID NO: 12. Library plaques were transferred to Hybond N+ nylon membranes (Amersham, Arlington Heights, Ill.). Screening of all cDNA and genomic libraries was performed according to standard protocols. Prehybridization and hybridizations were carried out in a solution of 40–50% formamide, 5× Denhardt's, 5× SSPE and 1.0% SDS at 42° C. Probes ([$^{32}$P]-labeled) were added at a concentration of $10^5$–$10^6$ cpm/ml of hybridization solution. Following 16–18 hours of hybridization, nylon membranes were washed extensively at room temperature in 2× SSPE with 0.1% SDS and subsequently exposed to X-ray film at −80° C. overnight. Positive plaques were subjected to one or more rounds of hybridization to obtain clonal phage. DNA prepared from lysate of the positive clones was subcloned into pBS+ and sequenced.

A first genomic clone encoding a rat ICAM-related domain 2 was identified that was determined to be homologous to domain 2 regions in other ICAM family members (see for example, Table 1 of U.S. patent application Ser. No. 08/102,852 now abandoned,), yet was distinct from the previously reported nucleotide sequences for rat ICAM-1 [Kita, et al., Biochem. Biophys. Acta 1131:108–110 (1992)] or mouse ICAM-2 [Xu, et al., J. Immunol. 149:2560–2565 (1992)]. The nucleic acid and deduced amino acid sequences for this clone were disclosed in the co-pending parents to the present application as purportedly variant forms of rat ICAM-3 and were set forth as SEQ ID NOS: 23 and 24, respectively, in U.S. Ser. No. 08/102,852 now abandoned. Herein, these same sequences are set out in SEQ ID NOS: 3 and 13, respectively.

A second, overlapping clone was also identified with the same probes and was determined to contain the ICAM domain 2 sequence of SEQ ID NO: 3 and 5' DNA encoding at least part of rat ICAM-1. The nucleic acid sequence for this clone was set forth in the co-pending parent to the present application as SEQ ID NO: 26 and is set forth herein as SEQ ID NO: 5. This second clone indicated that the ICAM-related gene fragment of the first clone and the gene encoding rat ICAM-1 are located on the same rat chromosome within 5 kb of each other.

B. Isolation of Rat ICAM-Related cDNA

In order to identify a more complete protein coding sequence for the ICAM-related polypeptide, [$^{32}$P]-labeled DNA encoding the domain 2 sequence from the rat genomic clone identified in Section A (SEQ ID NO: 3), supra, was used to screen a number of cDNA libraries from various rat and mouse cell types, including rat macrophage (Clontech, Palo Alto, Calif.), peripheral blood lymphocyte (PBL) (Clontech), T cell (constructed in-house), and spleen (Clontech), and mouse PBL (Clontech), T cell (constructed in-house), and B cell (constructed in-house).

A single clone was identified in a rat spleen cDNA library (Clontech) which contained five Ig-like domains, four of which were homologous to domains 2 through 5 in both ICAM-1 and ICAM-3. Moreover, this clone included 3' DNA encoding an apparent fifth Ig-like domain which had not been previously identified in any other ICAM polypeptide. In addition, the clone contained an unusual 3' sequence subsequently determined to be a partial intron (discussed infra) located between domains 4 and 5, suggesting that the clone was the product of an immature or aberrantly spliced transcript. The presence of the unique domain and the determination that the 3' region did not properly align with other known ICAMs suggested that the ICAM-related DNA potentially encoded a novel rat ICAM polypeptide. The nucleic acid sequence for this clone was set forth in the parent to the present application as SEQ ID NO: 25; herein the nucleic acid sequence for this spleen cDNA clone is set forth in SEQ ID NO: 6.

C. Re-analysis of Rat cDNA and Genomic DNAs

Subsequent to the Aug. 5, 1993 filing of U.S. patent application Ser. No. 08/102,852 now abandoned, it was determined that the partial rat spleen cDNA clone (SEQ ID NO: 25 in the parent and SEQ ID NO: 6 herein) and the rat liver genomic clone (SEQ ID NO: 26 of the parent and SEQ ID NO: 5 herein) were missing an internal 177 bp EcoRI fragment that was part of each of these clones but lost in a subcloning step when the library inserts were removed from the λ vector with EcoRI digestion and ligated into a sequencing vector. The observation that the cDNA and genomic clones might be missing a coding fragment became apparent upon alignment of the rat genomic and cDNA sequences with various RT-PCR amplification products, including SEQ ID NO: 7, which revealed a gap in the rat sequence.

Subsequent isolation and sequence alignment of a cDNA from a spleen library using the spleen cDNA clone (SEQ ID NO: 6) as a probe provided a first indication that a portion of the spleen cDNA and genomic clones were not sequenced. Further confirmation of this idea became apparent upon amplification of an RT-PCR fragment, spanning domains 3 through 5, using a 5' primer (RRD3 5'Xho, containing a 5' XhoI restriction site to facilitate cloning) set out in SEQ ID NO: 14, and a 3' primer (RRD5 3'Hind, containing a HindIII site to facilitate cloning) set out in SEQ ID NO: 15.

GAACTCGAGGCCATGCCTCCACTTTCC  (SEQ ID NO: 14)

CCATAAGCTTTATTCCACCGTGACAGCCAC (SEQ ID NO: 15)

Alignment of these two DNAs clearly revealed that the cDNA and genomic clones had lost a fragment prior to sequencing; this idea was further supported following sequencing of the RT-PCR DNA discussed infra. It was concluded that restriction digestion with EcoRI to remove the cDNA and genomic fragments prior to sequencing resulted in the excision of a 177 bp fragment that was not detected visually in the agarose gel separation of the clones from the λ phage sequences. Subsequent sequence analysis confirmed the location of two EcoRI sites flanking a 177 bp fragment in both of the original clones.

The 177 bp EcoRI fragment is situated between nucleotides 719 and 896 in the rat partial cDNA clone as set out in SEQ ID NO: 9 and between nucleotides 2812 and 2989 in the partial genomic clone as set out in SEQ ID NO: 8.

D. DNA Isolated by RT-PCR Clone

RT-PCR was utilized to generate more complete sequence information for the rat ICAM-related gene. Sequence information from the genomic clone (SEQ ID NO: 3) was used to design sense primers complementary to a region 5' of the protein coding region, as determined from the cDNA clone, and antisense primers designed complementary to coding sequences and regions 3' to the coding sequence in the cDNA clone (SEQ ID NO: 6).

Template cDNA for PCR reactions was prepared as follows. Approximately 2 μg of poly A+RNA isolated from rat spleen cells was denatured by heating at 65° C. in a 10 μl volume. Following denaturation, 0.1 μl RNasin (Invitrogen, San Diego, Calif.), 5 μl 5× RTase Buffer (BRL, Bethesda, Md.), 2 μl random hexamer (pd(N)6 at 100 μg/ml) (Pharmacia, Piscataway, N.J.), 6 μl dNTPs (2 mM each) and 2 μl AMV RTase (BRL) were added and the reaction was incubated at 42° C. for 60–90 min. Reactions were stored at −20° C. until needed.

An initial series of experiments was conducted to identify oligonucleotides primer pairs that produced an amplification product in PCR reactions using rat spleen cDNA as the template. Various 5' sense primers were paired in PCR with a 3' primer which was designed to be complementary to an internal, coding sequence; the 3' primer was designated RRD2 3-1 and is set forth in SEQ ID NO: 16.

AACGTGCGGAGCTGTCTG  (SEQ ID NO: 16)

(In the ultimately isolated RT-PCR product, SEQ ID NO: 7, infra, primer RRD2 3-1 corresponded to nucleotides 719 through 736.) Similarly, various 3' antisense primers were paired with a 5' primer designed complementary to another internal, coding sequence; the 5' primer in these reactions was designated RGen3900S and is set froth in SEQ ID NO: 17.

ACGGAATTCGAAGCCATCAACGCCAGG  (SEQ ID NO: 17)

(In SEQ ID NO: 7, infra, primer RGen3900S corresponded to nucleotides 1719 through 1736.) Based on the size of the amplification products and the ability of these products to hybridize with the partial cDNA clone, one pair of primers was determined to be most efficient and was used in subsequent PCR amplifications. The 5' primer was designated RGen780S (SEQ ID NO: 18) and the 3' primer was designated RGen4550AS (SEQ ID NO: 19).

CATGAATTCCGAATCTTGAGTGGGATG  (SEQ ID NO: 18)

ATAGAATTCCTCGGGACACCTGTAGCC  (SEQ ID NO: 19)

(In SEQ ID NO: 7, infra, primer RGen780S corresponded to nucleotides 1 through 18, and primer RGen4550AS corresponded to nucleotides 2197 through 2214.)

This primer pair was used in PCR under a variety of conditions to optimize amplification. A total of 15 different PCR buffers that varied in pH and $Mg^{++}$ concentration were used at two different annealing temperatures, and a sample of the product from each reaction was separated on a 1% agarose gel. Because no amplification product could be detected by visual inspection of the ethidium bromide stained gel from any of the reaction conditions, more sensitive Southern hybridization was employed to detect the PCR products.

Aliquots of the amplified DNA were separated by electrophoresis, transferred to a Hybond N+ nylon membrane using conventional Southern blotting wicking techniques, and hybridized with the entire rat cDNA which was $[^{32}P]$-labeled. Hybridization conditions were essentially as described for the library screening procedure in Section A, supra. Autoradiography indicated that a small amount of DNA of approximately 2.2 kb had been generated in two of the reactions, and the remainder of the amplification product from the two reactions was separated on an agarose gel. The 2.2 kb region was eluted from the gel, even though no band was evident upon visual inspection, and used as a template in another PCR reaction using the same primers (SEQ ID NOS: 18 and 19), Tris-HCl buffer, pH 8.0, containing 1 mM $Mg^{++}$, and 55° C. annealing temperature. The amplification product from the secondary PCR was visible in the gel and was eluted and cloned into a $pBS^+$ plasmid (Stratagene, La Jolla, Calif.) for sequence analysis.

The resulting RT-PCR clone was determined to contain 2214 bp as set forth in SEQ ID NO: 7. The clone encoded domains 2 through 6 found in the rat spleen cDNA clone, an additional amino terminal domain 1, an additional carboxy terminal domain 7, and 164 bp of what appeared to be a further carboxy terminal domain 8. Immediately 5' to domain 1 was an additional 144 bp sequence presumed to have been derived from an intron between the leader and the first domain. This clone did not contain a 5' leader sequence or 3' transmembrane and cytoplasmic regions. In addition to the previously identified domain 6 in the spleen cDNA clone, the 7th and 8th domains in the RT-PCR clone supported the hypothesis that this clone was a novel rodent ICAM.

EXAMPLE 2

Northern Blot Analysis

In order to further investigate the possibility that the ICAM-related clones identified in Example 1 encoded a novel ICAM polypeptide as suggested by the unique Ig-like domains, tissue specific expression was examined by Northern blot analysis to permit comparison with the previously reported expression patterns of human ICAMs [ICAM-1, Dustin, et al., *J. Immunol.* 137:245-254 (1986); ICAM-2, Staunton, et al., *Nature* 339:61-64 (1989); ICAM-3, de Fourgerolles and Springer, *J. Exp. Med.* 175:185-190 (1992)].

Total cellular RNA from rat lung, brain, spinal cord, liver, digestive tract, thymus, lymph nodes, and spleen was prepared using STAT60 RNA isolation reagents (Tel-test "B", Inc, Friendswood, Tex.) according to the manufacturer's suggested protocol. Poly A$^+$ RNA was purified from total RNA using oligo dT cellulose columns. Approximately 5 μg of RNA derived from each tissue was separated on a 1% formaldehyde agarose gel, and transferred to hybond-C nitrocellulose membranes (Amersham).

A fragment of the rat spleen cDNA from Example 1 corresponding to domains 2 through 4 (nucleotides 1 through 724 in SEQ ID NO: 6) was subcloned into pBluescript SK$^+$ (Stratagene) and an antisense riboprobe was generated by in vitro transcription using $^{32}$P-labeled UTP and approximately 500 ng of linearized template according to a manufacturer's (Boehringer Mannheim, Indianapolis, Ind.) suggested protocol. The membrane-bound RNA was prehybridized in a solution containing 50% formamide, 5× SSC, 1× PE (50 mM Tris-HCl, pH 7.5, 0.1% sodium pyrophosphate, 0.2% polyvinylpyrrolidone, 0.2% ficoll, 5 mM EDTA, 1% SDS) and 150 μg/ml denatured salmon sperm DNA. The radiolabeled probe was denatured by boiling and added to the prehybridization solution to a final concentration of 1×10$^6$ cpm/ml. Hybridization was allowed to proceed for 16-18 hours at 65° C. The membranes were then washed at 65° C. in 2× SSC containing 0.1% SDS and subsequently exposed to X-ray film for 3-16 hours.

The Northern blot analysis indicated that the ICAM-related cDNA identified in Example 1 was expressed only in rat brain, a tissue specificity not previously reported for any other ICAM polypeptides. This expression pattern, in combination with the unique Ig-like domains not known to exist in other ICAM polypeptides, indicated that the ICAM-related clone was a novel member of the ICAM family of proteins, and was named ICAM-4.

The fact that the initially identified cDNA clones were detected in a rat spleen library suggested that a subset of cells in the spleen may express ICAM-4 at low levels. However, a properly spliced clone could not be detected in numerous hemopoietic cDNA libraries which led to doubt if ICAM-4 protein is actually expressed in tissue other than brain. One explanation for the detection of ICAM-4 cDNA in spleen is that the sensitivity of PCR may have amplified a trace amount of transcript even though these tissues do not express the encoded protein.

EXAMPLE 3

Isolation of Full Length Rat ICAM-4 cDNA

A. Identification of a Rat Brain cDNA Clone

In view of the tissue specific expression of ICAM-4, brain tissue mRNA was utilized in an attempt to isolate a full length cDNA encoding ICAM-4. Two probes, one complementary to domains 1 through 2 and a second complementary to domains 3 through 5 of the spleen cDNA clone identified in Example 1 (SEQ ID NO: 7), were radiolabeled and used to screen a rat brain cDNA library in λgt10 which was previously constructed in-house. Hybridization conditions were as described in Example 1, and positive plaques were subjected to one or more rounds of screening to obtain clonal phage.

Nine positive clones were identified, two of which hybridized to both probes. The longest of the two clones, designated clone 7, contained 2550 bp encoding four of the five Ig-like domains found in the probe cDNA. In addition, clone 7 encoded four other Ig-like domains not found in the probe. Putative transmembrane and cytoplasmic domains were identified which were followed by a stop codon, a polyadenylation signal, and a poly A tail. Clone 7 was lacking at least one 5' Ig-like domain as determined by comparison to the RT-PCR clone (SEQ ID NO: 7), and also lacked a leader sequence; re-screening of the library did not yield any longer clones which contained these sequences. The nucleic acid sequence for clone 7 is set forth in SEQ ID NO: 10.

B. Determination of the 5' End

In order to isolate domain 1 and other 5' sequences, a PCR technique termed 5' Rapid Amplification of cDNA Ends (RACE) [*PCR Protocols: A Guide to Methods and Applications*, Innis, et al., (eds) Academic Press: New York (1990) pp:28-38] was employed using a 5' RACE kit (Clontech). This technique utilizes an internal primer paired with a second primer complementary to an adapter sequence ligated to the 5' end of cDNA library molecules. PCR with this primer pair will therefore amplify and facilitate identification of the intervening sequences. Overlapping sequence information can then be used to generate a complete sequence of the gene.

RACE-ready cDNA from rat brain (supplied with kit) was used in a PCR with the kit oligonucleotide and an antisense primer based on an internal ICAM-4 sequence. The 3' antisense primer, designated Spot714AS, was designed according to an ICAM-4 domain 4 sequence and is set forth in SEQ ID NO: 20.

CARGGTGACAAGGGCTCG        (SEQ ID NO: 20)

The amplification product resulting from this primer pair was subsequently subjected to a secondary PCR using the same 5' kit primer paired with a 3' primer complementary to a region in ICAM-4 domain 1. The second 3' primer was designated RRACE2 and is set forth in SEQ ID NO: 21.

TATGAATTCAGTTGAGCCACAGCGAGC        (SEQ ID NO: 21)

Each primer used in the secondary PCR contained an EcoR1 site to facilitate cloning of the resulting amplification products into pBS$^+$ (Stratagene). The resulting plasmid DNA which contained the 5' end of the gene was identified by hybridization to a rat ICAM-4 domains 1 and 2 probe, corresponding to nucleotides 1 through 736 in SEQ ID NO: 7. Partial sequence information for domain 1 and the hydrophobic leader was determined from the resulting amplification product.

The product from the 5' RACE method was a DNA fragment 222 bp long containing 60 bp upstream of the initiating methionine residue, an 82 bp leader sequence, and an 80 bp sequence from domain 1. The amplification product is set forth in SEQ ID NO: 11.

C. Full Length Sequence of Rat ICAM-4

A composite clone of the full length ICAM-4 was constructed from the sequence information derived from the 5' RACE method (SEQ ID NO: 11), the RT-PCR clone (SEQ ID NO: 7) and the brain cDNA clone 7 (SEQ ID NO: 10). The full length gene for rat ICAM-4 was determined to contain 2985 bp with a single open reading frame encoding a deduced 917 amino acid protein. A putative Kozak sequence is located upstream of the methionine residue in the leader sequence. A 27 amino acid hydrophobic leader sequence is followed by nine Ig-like domains, a transmembrane region and a 58 amino acid cytoplasmic tail. The composite ICAM-4 cDNA is set for in SEQ ID NO: 1, and the deduced amino acid sequence is set forth in SEQ ID NO: 2.

Like other ICAM polypeptides, ICAM-4 contains extracellular, transmembrane, and cytoplasmic domains. In the extracellular domain, the amino terminus of ICAM-4 is a leader sequence comprising amino acids 1 through 27 which is followed by nine immunoglobulin (Ig)-like domains, a characteristic unique to ICAM-4 in that ICAM-1, ICAM-2, and ICAM-3 contain five, two, and five extracellular Ig-like domain, respectively. In ICAM-4, domain 1 comprises amino acids 28 through 118; domain 2 comprises amino acids 119 through 224; domain 3 comprises amino acids 225 through $^{321}$; domain 4 comprises amino acids $^{322}$ through 405; domain 5 comprises amino acids 406 through 488; domain 6 comprises amino acids 489 through 569; domain 7 comprises amino acids 570 through 662; domain 8 comprises amino acids 663 through 742; and domain 9 comprises amino acids 743 through 830. Within each domain, a characteristic "loop" structure is formed by a disulfide bond between cysteine residues located generally at opposite ends of the domain amino acid sequence. Other structural features of ICAM-4 include the transmembrane region comprising amino acids 831 through 859 and the cytoplasmic region comprising amino acids 860 through 917.

Comparison of amino acid sequence homology of each domain in rat ICAM-4 with the other members of the ICAM family was limited to the corresponding sequences of human ICAM-1, ICAM-2, and ICAM-3 since sequence information for all three rodent homologs has not been previously reported. In the first domain, the rodent ICAM-4 shows 21, 30, and 28 percent identity with human ICAM-1, ICAM-2, and ICAM-3, respectively. The second domain is more conserved, with the amino acid percent identities being 60, 42 and 62 with ICAM-1, -2, and -3, respectively. Domains 3–5 show percent identities of 48, 49, and 40 with ICAM-1 and 60, 59 and 29 respectively for ICAM-3. Interestingly, rat ICAM-4 domains 6 through 8 are most homologous with domain 5 (ranging from 29–42% identical), possibly arising from a gene segment duplication event. The ninth and final extracellular domain aligns poorly with other ICAM domains but has 22% identity with the 3rd and 6th domains of human VCAM-1, another member of the Ig family of protein which participate in cell adhesion. The cytoplasmic tail is 58 amino acids long. This is longer than the other members of the ICAM family wherein human ICAM-1, -2, and -3 contain 28, 26, and 37 amino acids, respectively. As with the ninth domain, rat ICAM-4 cytoplasmic tail is most homologous with the cytoplasmic tail of human VCAM-1, which contains only 19 amino acids. The membrane proximal 19 amino acids of rat ICAM-4 share 7 amino acid residues with VCAM-1 (37%).

Finally, functional binding to LFA-1 (CD11a/CD18) maps to the first domain in the ICAMs. Vonderheide et al., [*J. Cell. Biol.*, 125:215–222 (1994)] identified a sequence motif purportedly involved in integrin binding. Despite the relatively low homology between rat ICAM-4 and other ICAMs in domain 1, this binding sequence motif is conserved, suggesting that rat ICAM-4 may be a ligand for LFA-1 and perhaps other integrins.

EXAMPLE 4

In situ Hybridization in Brain Tissue

In order to more localize the specific brain tissue which expressed ICAM-4, in situ hybridization with ICAM-4 domain 1 and ICAM-4 domains 3 through 4 anti-sense riboprobes was employed. The probes were labeled by in vitro transcription using $^{35}$S-labeled UTP.

Frozen tissue sections of normal rat brain were fixed in 4% paraformaldehyde for 20 minutes, rinsed and dehydrated, and the fixed RNA denatured for 2 minutes in 2× SSC, 70% formamide at 70° C. prior to hybridization. Tissue sections were hybridized overnight at 50° C. in a solution containing 50% formamide, 0.3M NaCl, 20 mM Tris-HCl, pH 7.4, 5 mM EDTA, 10% dextran sulfate, 1× Denhardt, 0.5 mg/ml yeast RNA, 100 mM DTT and a probe concentration of 50,000 cpm/µl. Slides were washed once in 4' SSC, 10 mM DTT at room temperature for 60 minutes, once in 50% formamide, 2× SSC, 10 mM DTT at 60° C. for 40 minutes, and once in each 2× SSC and 1× SSC for 30 minutes each at room temperature. Specificity of hybridization was determined in parallel experiments performed with the same protocol but also including a more stringent wash in 50% formamide, 1× SSC, 10 mM DTT at 60° C. for 40 minutes. After washing, the slides were dipped in NTB2 emulsion (Kodak, Rochester, N.Y.) and exposed from 2 to 21 days before being developed and counter-stained. Negative controls included sense probes generated from ICAM-4 domain 1 and ICAM-4 domain 3 through 4 sense riboprobes, in addition to a human immunodeficiency virus (HIV-1) riboprobe.

The signal detected in brain tissue was primarily localized in the gray matter with the strongest signal in the cerebral cortex and hippocampus. The hybridization profile was consistent with ICAM-4 expression primarily in cerebral neurons.

EXAMPLE 5

Generation of ICAM-4 fusion proteins

Rat ICAM-4/glutathione S-transferase (GST) fusion proteins were generated using the prokaryote expression vector pGEX (Pharmacia, Alameda, Calif.) in order to generate monoclonal antibodies against specific ICAM-4 polypeptide fragments.

PCR primers corresponding to the 5' and 3' ends of domain 1 and the 5' and 3' ends of domain 2 were used to amplify DNA fragments encoding the individual domains. The resulting fragments were separately cloned into an EcoRI site of pGEX-2T; DNA sequence analysis confirmed the correct orientation and reading frame. Transformants were subsequently screened for their ability to produce fusion protein of the appropriate molecular weight.

Both ICAM-4 domain 1/GST and ICAM-4 domain 2/GST fusion proteins remained in the insoluble fraction after the bacteria were lysed by sonication in PBS containing 1% SDS. The insoluble protein fraction from 100 ml cultures were boiled in SDS loading dye and separated on a 10% preparative polyacrylamide-SDS gel. The gel was stained in ice cold 0.4M KCl and the fusion protein bands were excised. Fusion proteins were electroeluted from the gel slices in dialysis tubing in buffer containing 25 mM Tris-HCl and 192 mM glycine. Approximate protein concentration was determined by $OD_{280}$ and purity of the preparation was determined on SDS-PAGE stained with Coomasie blue.

EXAMPLE 6

Monoclonal Antibody Production

Balb/c mice were immunized by subcutaneous injection with 40–50 µg ICAM-4 domain-2/GST fusion protein (described in example 5) emulsified in Freund's complete adjuvant (FCA). Two weeks later, the mice were again immunized by subcutaneous injection with the same protein, emulsified however in Freund's incomplete adjuvant. Two final intraperitoneal immunizations given two weeks after the second immunization included soluble antigen with no adjuvant given at two week intervals. Serum from each immunized mouse was assayed by ELISA for its ability to specifically react with rat ICAM-4 produced by the baculovirus expression system described infra.

The spleen from mouse #1654 was sterilely removed and placed in 10 ml serum-free RPMI 1640. A single-cell suspension was formed by grinding the spleen tissue between frosted ends of two glass microscope slides submerged in serum free RPMI 1640 (Gibco, Burlington, Ottawa, Canada) supplemented with 2 mM L-glutamine, 1 mM sodium pyruvate, 100 units/ml penicillin, and 100 µg/ml streptomycin. The cell suspension was filtered through a sterile 70-mesh Nitex cell strainer (Becton Dickinson, Parsippany, N.J.), and washed twice with RPMI followed by centrifuging at 200×g for 5 minutes. The resulting pellet from the final wash was resuspended in 20 ml serum-free RPMI. Thymocytes taken from three naive Balb/c mice were prepared in an identical manner.

Prior to fusion, NS-1 myeloma cells were maintained in log phase growth in RPMI with 11% Fetalclone serum (FBS) (Hyclone Laboratories, Logan, Utah) for three days. Once harvested, the cells were centrifuged at 200×g for 5 minutes, and the pellet was washed twice as described in the foregoing paragraph. After washing, the cell suspension was brought to a final volume of 10 ml in serum free RPMI. A 20 µl aliquot was removed and diluted 1:50 with serum free RPMI, and a 20 µl aliquot of this dilution was removed, mixed with 20 µl 0.4% trypan blue stain in 0.85% saline (Gibco), loaded onto a hemacytometer (Baxter Healthcare, Deerfield, Ill.) and the cells counted. Approximately $2.425 \times 10^8$ spleen cells were combined with $4.85 \times 10^7$ NS-1 cells, the mixture centrifuged and the supernatant removed. The resulting pellet was dislodged by tapping the tube and 2 ml of 50% PEG 1500 in 75 mM Hepes, pH 8.0, (Boehringer Mannheim, Indianapolis, Ind.) was added with stirring over the course of 1 minute. Subsequently, an additional 14 ml serum free RPMI was added over 7 minutes. The cell suspension was centrifuged at 200×g for 10 minutes and the supernatant discarded. The pellet was resuspended in 200 ml RPMI containing 15% FBS, 100 µM sodium hypoxanthine, 0.4 µM aminopterin, 16 µM thymidine (HAT) (Gibco), 25 units/ml IL-6 (Boehringer Mannheim) and $1.5 \times 10^6$ thymocytes/ml. The suspension was first placed in a 225 cm² flask (Corning, Essex, United Kingdom) at 37° C. for four hours before being dispensed into ten 96-well flat bottom tissue culture plates (Corning) at 200 µl/well. Cells in the plates were fed on days 3, 4, 5, and 6 post fusion by aspirating approximately 100 µl from each well with a 20 G needle (Becton Dickinson), and adding 100 µl/well plating medium described above except containing 10 units/ml IL-6 and lacking thymocytes.

The fusion plates were screened initially by antigen capture ELISA as follows. Immulon 4 plates (Dynatech, Cambridge, Mass.) were coated overnight at 4° C. with 100 ng/well of either domain 1-GST or domain 2-GST fusion protein in 50 mM carbonate buffer. The plates were blocked with 100 µl/well 0.5% fish skin gelatin (Sigma, St. Louis, Mo.) in PBS for 30 minutes at 37° C. After blocking, the plates were washed 3× with PBS containing 0.05% Tween 20 (PBST) and 50 µl/well of hybridoma supernatant from each fusion was added. After incubation at 37° C. for 30 minutes, the plates were washed as described above, and 50 µl of a 1:3500 dilution of horseradish peroxidase-conjugated goat anti-mouse IgG (Fc) (Jackson ImmunoResearch, West Grove, Pa.) was added. Plates were again incubated for 30 minutes and washed 4× with PBST. Substrate, 100 µl/well, consisting of 1 mg/ml o-phenylene diamine (Sigma) and 0.1 µl/ml 30% $H_2O_2$ in 100 mM citrate, pH 4.5, was added. The color reaction was allowed to proceed 10 minutes and quenched with the addition of 50 µl/well of 15% $H_2SO_4$. Absorbance at 490 nm was then determined on an automated plate reader (Dynatech).

Wells which were positive for domain 2-GST protein, but not for domain 1-GST protein, were then screened by ELISA against a Baculovirus supernatant (described infra). ELISA was performed as described above except that the Immulon 4 plates were initially coated overnight with Baculovirus supernatant diluted 1:4 in 50 mM carbonate buffer. Three wells (103A, 103B and 103F) were cloned two to three times, successively, by doubling dilution in RPMI, 15% FBS, 100 µM sodium hypoxanthine, 16 µM thymidine, and 10 units/ml IL-6. Wells of clone plates were scored visually after 4 days and the number of colonies in the least dense wells was recorded. Selected wells of each cloning were again assayed by ELISA after 7 to 10 days against either domain 1-GST protein and domain 2-GST protein, or Baculovirus supernatant.

The monoclonal antibodies produced by the hybridomas were isotyped by ELISA. Immulon 4 plates (Dynatech) were coated at 4° C. with 50 µl/well goat anti-mouse IgA, IgG, or IgM (Organon Teknika, Durham, N.C.) diluted 1:5000 in 50 mM carbonate buffer, pH 9.6. Wells were blocked for 30 minutes at 37° C. with 1% BSA in PBS, washed 3× with PBST. A 1:10 dilution of hybridoma culture supernatant (50 µl) was added to each plate, incubated, and washed as above. After removal of the last wash, 50 µl horseradish peroxidase-conjugated rabbit anti-mouse $IgG_1$, $G_{2a}$, $G_{2b}$, or $G_3$ (Zymed, San Francisco, Calif.) (diluted 1:1000 in PBST with 1% normal goat serum) was added. Plates were incubated as above, washed 4× with PBST and 100 µl substrate, was added. The color reaction was quenched after 5 minutes with addition of 50 µl 15% $H_2SO_4$, and absorbance at 490 nm determined on a plate reader (Dynatech).

Results indicated that all three antibodies were $IgG_1$ isotype. These antibodies were subsequently used in immunocytochemical analyses, Western blotting, and for purification of protein expressed in baculovirus.

EXAMPLE 7

Baculovirus expression

A baculovirus expression system (Invitrogen) was used to generate soluble protein corresponding to domains 1 through 6 of ICAM-4. Because the leader sequence for ICAM-4 was not known at the time, the expression construct was made containing the coding sequence for ICAM-4 fused 3' to the ICAM-1 leader sequence in proper reading frame. Specific details regarding construction of the ICAM-I/ICAM-4 expression plasmid is as follows.

Rat ICAM-1 DNA encoding the five Ig-like domains was amplified by PCR using primers which incorporated several features to facilitate construction of the fusion plasmid. The 5' oligonucleotide primer included HindIII and BglII sites, in addition to a consensus Kozak sequence upstream of the first methionine in the leader sequence. The 3' oligonucleotide primer included a coding sequence for six histidines followed by a stop codon and a HindIII cloning site. The PCR amplification product was cloned into a HindIII-digested pBS+ vector and sequence analysis confirmed the appropriate construction. An internal SmaI site in the ICAM-1 leader sequence and another SmaI site in the vector's multiple cloning region (3' to ICAM-1 Ig-like domain 5) were digested which removed most of the ICAM-1 coding sequence. After these manipulations, the linearized, blunt-ended vector contained a portion of the upstream multiple cloning region (those restriction sites 5' of the original HindIII site in the multiple cloning region), the Kozak sequence and most of the ICAM-1 leader sequence.

The coding sequence for rat ICAM-4 domains 1 through 6 was amplified by PCR utilizing primers designed to permit cloning of this sequence into the linearized vector described above. The 5' oligonucleotide primer included an EcoRV site and the codons needed to complete the ICAM-1 leader sequence. The 3' oligonucleotide primer included codons for six histidine residues, a stop codon, and HindIII and EcoRV restriction sites. The amplification product from this PCR was digested with EcoRV to produce a blunt-ended sequence which was then ligated into the blunt-ended SmaI-digested pBS+ linearized vector. The entire sequence containing the ICAM-1 leader sequence 5' to the ICAM-4 domains 1 through 6 was removed from the construct with BglII and HindIII digestion and the purified ICAM-1/ICAM-4 fusion sequence cloned directly into a BglII/HindIII-digested pBluesac III vector (Invitrogen).

Protein production by the recombinant virus was assayed for by ELISA, initially using immune sera from mice immunized with rat ICAM-4 domain-2/GST fusion protein described in Example 5. In later work, monoclonal antibodies generated from those mice were used to purify ICAM-4 protein produced by the recombinant baculovirus in SF9 cells.

EXAMPLE 8

Immunocytochemistry

Immunocytochemistry with monoclonal antibody 103A was performed to localize the protein production within the rat brain.

A brain was harvested from a normal adult female Lewis rat, sagittally sectioned, and washed in RNase-free 1× PBS on ice for 30 min. The brain sections were then placed in Tissue Tek II cryomolds (Miles Laboratories, Inc., Naperville, Ill.) with a small amount of O.C.T. compound (Miles, Inc., Elkhart, Ind.). The brains were centered in the cryomold, the cryomold filled with OCT compound, then placed in a container with 2-methylbutane (Aldrich Chemical Company, Inc., Milwaukee, Wis.) and the container placed in liquid nitrogen. Once the tissue and OCT compound in the cryomold were frozen, the blocks were stored at −80° C. until sectioning.

The tissue was sectioned at 6 μm thickness, adhered to Vectabond (Vector Laboratories, Inc., Burlingame, Calif.) coated slides and allowed to air-dry at room temperature overnight until use. The sections were fixed in ethyl ether (Malinckrodt, Pads, Ky.) for 5 minutes at room temperature. Once the slides were removed from the ether, the reagent was allowed to evaporate. Each tissue section was blocked with 150 μl 50% Normal rat serum (Sigma) and 2% bovine serum albumin (BSA) (Sigma) in 1× PBS (made with sodium phosphates only) for 30 minutes at room temperature. After blocking, the solution was gently blotted from the sections and the purified supernatant antibody 103A (1.65 mg/ml) was diluted 1:10 in the blocking solution and 150 μl applied to each tissue section. The slides were placed in a humidity chamber and incubated at 4° C. overnight.

The next day the antibody solution was blotted gently from the section and the slides washed 3 times in 1× PBS for 4 minutes in each wash. The excess PBS was aspirated from the slide and 100 μl of the secondary, rat anti mouse-biotin conjugated antibody (Jackson ImmunoResearch Laboratories), diluted 1:100 in a solution of 10% normal rat serum and 2% BSA in 1× PBS, applied to the tissues. Incubation was allowed to proceed for 1 hour at room temperature. The sections were washed 2 times in 1× PBS for 4 minutes in each wash, then 100 μl of ABC reagent from an Elite Rat IgG Vectastain ABC kit (Vector Laboratories, Inc., Burlingame, Calif.), prepared according to the product insert, was applied to each section. Incubation was allowed to proceed for 30 minutes at room temperature. After incubation, the slides were washed 2 times in 1× PBS (4 minutes each wash) and 150 μl of Vector VIP Peroxidase Substrate Solution (Vector Laboratories, Inc., Burlingame, Calif.) applied to each section for approximately 10 minutes. After color development, the sections were rinsed under running tap water for 5 minutes, counterstained with Mayer's hematoxylin (Sigma) for 20 seconds, and rinsed again in gently running tap water for 5 minutes. The slides were dehydrated across a graded series of ethanols, passed through xylene and mounted with Accumount 60 (Stephens Scientific, Riverdale, N.J.).

Immunohistochemistry of rat brain sections strained with mAb 103A indicated that rat ICAM-4 is expressed in the neuronal cells of the hippocampus. Staining pattern suggested that the protein might be limited to the neuronal processes (dendrites). Brain sections stained in a similar manner with an irrelevant antibody or second step reagent alone do not show the distinct expression pattern seen with MAb 103A.

EXAMPLE 9

Cloning of a Human ICAM-4 DNA

During the cloning of rat ICAM-4 out of genomic DNA, it was discovered that ICAM-4 and ICAM-1 were located within 5 kb of each other and this information was utilized in an attempt to clone the human homologue of ICAM-4.

Genome Systems Inc. (St. Louis, Mo.) amplified fragments in a human P1 library by PCR using human ICAM-1 domain 3 primers, a sense primer designed complementary to human ICAM-1 domain 3 (H-1/D3 S) and an antisense primer designed complementary to human ICAM-1 domain 3 (H-1/D3 AS). These primers are set forth in SEQ ID NOs: 22 and 23, respectively.

| | |
|---|---|
| CCGGGTCCTAGAGGTGGACACGCA | (SEQ ID NO: 22) |
| TGCAGTGTCTCCTGGCTCTGGTTC | (SEQ ID NO: 23) |

Two clones, designated 1566 and 1567, were identified and subjected to further analysis. Both P1 clones contained approximately 75–95 kb genomic DNA inserts. The clones were digested with BamH1, separated with agarose gel electrophoresis, and blotted onto nylon membranes. Southern blots hybridization were performed under either low stringency (30% formamide) or high stringency (60% formamide) at 42° C. with human ICAM-1, ICAM-3 or rat ICAM-4 radiolabeled probes; other constituents of the hybridization solution were as described in Example 1. The low stringency hybridization series was washed at room temperature in 2× SSPE containing 0.1% SDS. The high stringency hybridization was washed at 65° C. in 0.2× SSPE containing 0.1% SDS. The washed membranes were exposed to X-ray film for 3.5 hours.

The differential hybridization indicated that human ICAM-1 was contained on a 5.5 kb BamH1 fragment while human ICAM-3 was located on a 4.0 kb and a 1.5 kb BamH1 fragment. The human ICAM-1 and ICAM-3 fragments were subcloned into pBS+ and their identity confirmed by limited sequence analysis.

A 7.0 kb BamH1 fragment that hybridized with rat ICAM-4 under high stringency conditions was subcloned and further fragmented with RsaI restriction digestion. Three RsaI fragments that hybridized with rat ICAM-4 were identified and their sequences determined. Based on homology to rat ICAM-4, these fragments appeared to contain domains 2, 3, 4, 5 and part of domain 6. These genomic fragments are currently being used to screen human brain cDNA libraries for the expressed version of this gene. Also, a multiple tissue Northern is planned.

What is claimed is:

1. A purified and isolated polynucleotide comprising the ICAM-4 protein coding sequence set out in SEQ ID NO: 1.

2. The polynucleotide of claim 1 which is a DNA molecule.

3. The DNA molecule of claim 2 which is a cDNA molecule.

4. The DNA molecule of claim 2 which is a wholly or partially chemically synthesized DNA molecule.

5. A purified and isolated DNA molecule consisting of a nucleotide sequence which encodes the ICAM-4 amino acid sequence set out in SEQ ID NO: 2.

6. The DNA molecule of claim 5 which is a genomic DNA molecule.

7. A DNA expression construct comprising a DNA molecule according to claim 2 or 5.

8. A host cell transformed with a DNA molecule according to claim 2 or 5.

9. A method for producing an ICAM-4 polypeptide comprising growing a host cell according to claim 8 in a suitable medium, isolating ICAM-4 polypeptide from said host cell or the medium of its growth, and recovering said ICAM-4 polypeptide.

* * * * *

UNITED STATES PATENT AND TRADEMARK OFFICE
CERTIFICATE OF CORRECTION

PATENT NO.    :   5,700,658
DATED         :   December 23, 1997
INVENTOR(S)   :   Kilgannon et al.

It is certified that error appears in the above-identified patent and that said Letters Patent is hereby corrected as shown below:

Col. 7, line 31: Please delete "SEQ ID NO. 1 1", and insert --SEQ ID NO. 11--.

Col. 10, line 15: Please delete "CATGAATF", and insert - -CATGAATT- -.

Col. 13, line 17: Please delete "$^{321}$", and insert - -321- -.

Col. 13, line 17: Please delete "$^{322}$", and insert - -322- -.

Col. 14, line 13: Please delete "4'", and insert - -4X--.

Col. 17, line 59: Please delete "Pads", and insert - -Paris--.

Signed and Sealed this

Twenty-eighth Day of November, 2000

Attest:

Q. TODD DICKINSON

*Attesting Officer*     *Director of Patents and Trademarks*